US011000468B2

(12) United States Patent
Sturgis et al.

(10) Patent No.: US 11,000,468 B2
(45) Date of Patent: May 11, 2021

(54) AEROSOL COMPOSITIONS (71) Applicant: The Procter & Gamble Company, Cincinnati, OH (US)

(72) Inventors: David Arthur Sturgis, Montgomery, OH (US); Jianjun Justin Li, West Chester, OH (US); Marc Adam Flickinger, West Chester, OH (US); Virginia Tzung-Hwei Hutchins, Cincinnati, OH (US); Steven Louis Diersing, Cincinnati, OH (US); Steven Michael Wujek, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/696,274

(22) Filed: Sep. 6, 2017

(65) Prior Publication Data
US 2018/0064623 A1 Mar. 8, 2018

Related U.S. Application Data (60) Provisional application No. 62/383,670, filed on Sep. 6, 2016.

(51) Int. Cl.
*A61K 8/73* (2006.01)
*A61Q 13/00* (2006.01)
*A61K 8/04* (2006.01)
*C11B 9/00* (2006.01)
*A61K 8/34* (2006.01)
(Continued)

(52) U.S. Cl.
CPC .............. *A61K 8/738* (2013.01); *A61K 8/046* (2013.01); *A61K 8/33* (2013.01); *A61K 8/34* (2013.01); *A61K 8/347* (2013.01); *A61K 8/37* (2013.01); *A61K 8/44* (2013.01); *A61K 8/498* (2013.01); *A61K 8/4973* (2013.01); *A61Q 13/00* (2013.01); *A61Q 15/00* (2013.01); *C11B 9/0015* (2013.01);
(Continued)

(58) Field of Classification Search
CPC ....................................................... A61K 8/738
See application file for complete search history.

(56) References Cited

U.S. PATENT DOCUMENTS 4,049,792 A 9/1977 Elsnau
4,731,243 A 3/1988 Lindauer
(Continued)

FOREIGN PATENT DOCUMENTS

EP 0392608 B1 6/1995
EP 1024785 B1 1/2003
(Continued)

OTHER PUBLICATIONS

14489 PCT International Search Report dated Oct. 30, 2017 (12 pages).
(Continued)

*Primary Examiner* — Arrie L Reuther
(74) *Attorney, Agent, or Firm* — Kathleen Y. Carter (57) ABSTRACT A personal aerosol composition including a solvent, a cyclodextrin perfume complex, and a propellant, where the cyclodextrin perfume complex includes 10% or more perfume raw materials, by weight of the perfume, having: a cyclodextrin complex stability constant of about 3.0 or less, a C log P of about 2.5 or less; and a weight average molecular weight of about 200 Daltons or less.

11 Claims, 4 Drawing Sheets (51) Int. Cl.
*A61K 8/37* (2006.01)
*A61K 8/33* (2006.01)
*A61K 8/44* (2006.01)
*A61Q 15/00* (2006.01)
*A61K 8/49* (2006.01)

(52) U.S. Cl.
CPC .......... *C11B 9/0019* (2013.01); *C11B 9/0061* (2013.01); *A61K 2800/56* (2013.01)

(56) References Cited

U.S. PATENT DOCUMENTS

| | | | |
|---|---|---|---|
| 4,803,195 | A | 2/1989 | Holzner |
| 4,904,307 | A | 2/1990 | Ammeraal |
| 5,094,761 | A | 3/1992 | Trinh |
| 5,135,747 | A | 8/1992 | Faryniarz |
| 5,176,903 | A | 1/1993 | Goldberg |
| 5,378,468 | A | 1/1995 | Suffis |
| 5,380,707 | A | 1/1995 | Barr |
| 5,403,828 | A | 4/1995 | Lewis |
| 5,429,816 | A | 7/1995 | Hofrichter et al. |
| 5,508,259 | A | 4/1996 | Holzner |
| 5,543,157 | A | 8/1996 | Trinh |
| 5,580,851 | A | 12/1996 | Trinh |
| 5,626,856 | A | 5/1997 | Berndt |
| 5,660,845 | A | 8/1997 | Trinh |
| 5,711,941 | A | 1/1998 | Behan |
| 5,714,445 | A | 2/1998 | Trinh |
| 5,718,887 | A | 2/1998 | Wolf et al. |
| 5,723,420 | A | 3/1998 | Wei |
| 5,733,272 | A | 3/1998 | Brunner |
| 5,780,020 | A | 7/1998 | Peterson |
| 5,840,287 | A | 11/1998 | Guskey et al. |
| 5,840,289 | A | 11/1998 | Hall |
| 5,861,144 | A | 1/1999 | Peterson et al. |
| 5,874,067 | A | 2/1999 | Lucas |
| 5,879,666 | A | 3/1999 | Lucas |
| 5,882,638 | A | 3/1999 | Dodd |
| 5,897,854 | A | 4/1999 | Lucas |
| 5,897,855 | A | 4/1999 | Trinh |
| 5,932,198 | A | 8/1999 | Goldman |
| 5,932,199 | A | 8/1999 | Esser |
| 5,968,489 | A | 10/1999 | Swaile et al. |
| 5,976,514 | A | 11/1999 | Guskey |
| 6,013,248 | A | 1/2000 | Luebbe et al. |
| 6,036,964 | A | 3/2000 | Guenin |
| 6,077,318 | A * | 6/2000 | Trinh .................. A61L 9/01 252/8.91 |
| 6,110,449 | A | 8/2000 | Bacon et al. |
| 6,123,932 | A | 9/2000 | Guskey et al. |
| 6,165,452 | A | 12/2000 | Boden |
| 6,180,121 | B1 | 1/2001 | Guenin |
| 6,287,603 | B1 | 9/2001 | Prasad et al. |
| 6,306,818 | B1 | 10/2001 | Anderson |
| 6,352,688 | B1 | 3/2002 | Scavone et al. |
| 6,495,097 | B1 | 12/2002 | Streit |
| 6,509,010 | B2 | 1/2003 | Beck |
| 6,793,915 | B1 | 9/2004 | Guenin |
| 6,805,855 | B2 | 10/2004 | Mattai |
| 6,824,763 | B2 | 11/2004 | Brooks |
| 6,835,373 | B2 | 12/2004 | Kolodzik et al. |
| 6,869,923 | B1 | 3/2005 | Cunningham |
| 6,893,647 | B1 * | 5/2005 | Malton .................. A61K 8/738 424/401 |
| 6,936,242 | B2 | 8/2005 | Elliott et al. |
| 7,041,337 | B2 | 5/2006 | Heltovics et al. |
| 7,208,462 | B2 | 4/2007 | Heltovics et al. |
| 7,208,463 | B2 | 4/2007 | Heltovics et al. |
| 7,208,464 | B2 | 4/2007 | Heltovics et al. |
| 7,208,465 | B2 | 4/2007 | Heltovics et al. |
| 7,407,650 | B2 | 8/2008 | Heltovics et al. |
| 7,413,731 | B2 | 8/2008 | Heltovics et al. |
| 8,147,808 | B2 * | 4/2012 | Scavone .................. A61K 8/26 424/65 |
| 8,632,755 | B2 * | 1/2014 | Scavone .................. A61K 8/26 424/400 |
| 9,222,055 | B2 | 12/2015 | Fraser |
| 9,649,386 | B2 | 5/2017 | Scavone et al. |
| 9,649,387 | B2 | 5/2017 | Scavone |
| 10,149,910 | B2 | 12/2018 | Scavone |
| 10,351,796 | B2 | 7/2019 | Sturgis |
| 2002/0007055 | A1 | 1/2002 | Uchiyama et al. |
| 2002/0025946 | A1 | 2/2002 | Buchanan |
| 2003/0049290 | A1 | 3/2003 | Jha |
| 2003/0060379 | A1 | 3/2003 | Souter et al. |
| 2003/0069165 | A1 | 4/2003 | Malton et al. |
| 2003/0087776 | A1 | 5/2003 | Heltovics |
| 2003/0119713 | A1 | 6/2003 | Heltovics |
| 2003/0194416 | A1 | 10/2003 | Shefer |
| 2003/0198680 | A1 | 10/2003 | Shefer |
| 2003/0211125 | A1 | 11/2003 | Heltovics |
| 2003/0232025 | A1 | 12/2003 | Colwell |
| 2003/0232730 | A1 | 12/2003 | Holland et al. |
| 2004/0001891 | A1 | 1/2004 | Smith |
| 2004/0077520 | A1 | 4/2004 | Foley |
| 2004/0091435 | A1 | 5/2004 | Shefer |
| 2004/0109833 | A1 | 6/2004 | Tang |
| 2004/0175404 | A1 | 9/2004 | Shefer |
| 2004/0202632 | A1 | 10/2004 | Gott |
| 2005/0003975 | A1 | 1/2005 | Browne |
| 2006/0159639 | A1 | 7/2006 | Ogura |
| 2006/0243322 | A1 | 11/2006 | Heltovics et al. |
| 2006/0263236 | A1 * | 11/2006 | Woo .................. A61L 9/14 422/5 |
| 2006/0263313 | A1 | 11/2006 | Scavone |
| 2006/0292098 | A1 | 12/2006 | Scavone |
| 2007/0166254 | A1 | 7/2007 | Bianchi |
| 2007/0248553 | A1 | 10/2007 | Scavone et al. |
| 2008/0087776 | A1 | 4/2008 | Chuang |
| 2008/0194454 | A1 | 8/2008 | Morgan |
| 2008/0213191 | A1 | 9/2008 | Scavone et al. |
| 2008/0213203 | A1 | 9/2008 | Seavone |
| 2008/0213204 | A1 | 9/2008 | Scavone et al. |
| 2008/0215023 | A1 | 9/2008 | Scavone et al. |
| 2008/0241201 | A1 | 10/2008 | Warr et al. |
| 2009/0010972 | A1 | 1/2009 | Modafari et al. |
| 2009/0029020 | A1 | 1/2009 | Strassburger |
| 2009/0084513 | A1 | 4/2009 | Barnholtz et al. |
| 2009/0214446 | A1 | 8/2009 | Strassburger |
| 2009/0218057 | A1 | 9/2009 | Manifold et al. |
| 2009/0218058 | A1 | 9/2009 | Manifold et al. |
| 2010/0226871 | A1 | 9/2010 | Fraser et al. |
| 2011/0183132 | A1 | 7/2011 | Manifold et al. |
| 2012/0087828 | A1 * | 4/2012 | Uchiyama .................. A61L 9/14 422/5 |
| 2013/0302566 | A1 | 11/2013 | Barnholtz et al. |
| 2014/0274870 | A1 * | 9/2014 | Cetti .................. C11B 9/0069 512/2 |
| 2018/0064588 | A1 | 3/2018 | Sturgis |
| 2018/0064623 | A1 | 3/2018 | Sturgis |
| 2018/0064624 | A1 | 3/2018 | Sturgis |
| 2018/0066206 | A1 | 3/2018 | Horenziak |
| 2018/0066207 | A1 | 3/2018 | Sturgis |
| 2019/0292488 | A1 | 9/2019 | Sturgis |

FOREIGN PATENT DOCUMENTS

| | | |
|---|---|---|
| EP | 0535942 B2 | 11/2004 |
| JP | S6335517 A | 2/1988 |
| JP | H03259986 A | 11/1991 |
| JP | H10120541 A | 5/1998 |
| JP | H10263062 A | 10/1998 |
| JP | H11209784 A | 8/1999 |
| JP | 2001316219 A | 11/2001 |
| JP | 2002037722 A | 2/2002 |
| JP | 20150070937 | 6/2015 |
| WO | WO9856340 A1 | 12/1998 |
| WO | 0234227 A1 | 5/2002 |
| WO | WO02069924 A1 | 9/2002 |

(56) References Cited

OTHER PUBLICATIONS

All Office Actions, U.S. Appl. No. 11/712,771.
14486 PCT International Search Report, dated Nov. 28, 2017 (14 pages).
14488 PCT International Search Report, dated Dec. 1, 2017 (12 pages).
Del Valle, E. M. Martin; Cyclodextrins and their uses: a review; Process Biochemistry; vol. 39; 2004; pp. 1033-1046.
Hedges, Allan R.; Industrial Applications of Cyclodextrins; Chem. Rev. 1998; vol. 98; pp. 2035-2044.
All Office Actions; U.S. Appl. No. 15/696,268.
All Office Actions; U.S. Appl. No. 15/696,282.
All Office Actions; U.S. Appl. No. 16/429,683.

* cited by examiner

AEROSOL COMPOSITIONS

CROSS REFERENCE TO RELATED APPLICATION

This application claims the benefit of U.S. Provisional Application No. 62/383,670, filed Sep. 6, 2016, the substance of which is incorporated herein by reference.

FIELD OF THE INVENTION

This application generally relates to aerosol compositions comprising cyclodextrin perfume complexes.

BACKGROUND OF THE INVENTION

Perfume compositions are utilized to help make products, like personal aerosol products, more delightful to consumers. This is especially true for perfume compositions and cyclodextrin perfume complexes that can provide a desired and long-lasting perfume or scent each time the composition is applied or used. However, current perfume compositions utilized in aerosol compositions are not optimized for release from a cyclodextrin complex and some components can remain within the complex and unexpressed. As such, there is a need for a perfume composition which is optimized for release from a cyclodextrin and cyclodextrin perfume complexes made from such optimized perfumes.

SUMMARY OF THE INVENTION

Included herein, for example, is a personal aerosol composition, comprising a solvent, a cyclodextrin perfume complex, and a propellant, wherein the cyclodextrin perfume complex comprises a cyclodextrin and a perfume comprising perfume raw materials, wherein 10% or more, by weight of the perfume, of the perfume raw materials have: a) a cyclodextrin complex stability constant of about 3.0 or less, b) a C log P of about 2.5 or less; and c) a weight average molecular weight of about 200 Daltons or less.

Also included herein, for example, is a personal aerosol composition, comprising a solvent, a cyclodextrin perfume complex, and a propellant, wherein the cyclodextrin perfume complex comprises a cyclodextrin and a perfume comprising perfume raw materials, wherein 20% or more, by weight of the perfume, of the perfume raw materials, are selected from the group consisting of: ethyl-2-methyl butyrate; beta gamma hexanol; iso amyl acetate; amyl acetate; cis-3-hexenyl acetate; gamma-octalactone; ethyl vanillin; vanillin; benzaldehyde; dimethyl anthranilate; iso-eugenyl acetate; canthoxal; 3,6-nonadien-1-ol; triplal; and combinations thereof.

These and other combinations are possible and are described in more detail below.

DETAILED DESCRIPTION OF THE INVENTION

"Cyclodextrin complex stability constant" or "complex stability constant" (log K) refers to the ability of a perfume raw material to bind to a cyclodextrin. The complex stability constant of a multitude of materials with respect to various cyclodextrins as measured by the calorimetry technique can be found in the literature, for example, Rekharsky and Inoue (1998), Complexation Thermodynamics of Cyclodextrins, Chemical Review, 98, 1875-1917. In addition, for reference, a list of perfume raw materials and their estimated complex stability constants is included in a table below.

"C log P" refers to calculated log P values, which is a measure of a compound's hydrophilicity, wherein log P is the octanol water partitioning coefficient as computed by the Consensus algorithm implemented in ACD/Percepta version 14.02 by Advanced Chemistry Development, Inc. (ACD/Labs, Toronto, Canada).

"Odor Detection Threshold" refers to the lowest concentration in the air of a certain odor compound that is perceivable to the human sense of smell. The Odor detection Threshold of a multitude of materials can be found in van Gemert, L. J.; *Odour Thresholds Compilations of Odour Threshold Values in Air, Water and Other Media*; Oliemans Punter & Partners; The Netherlands, 2011. It is in units of –log molar concentration. In this context, human odor detection thresholds (ODTs) are expressed as olfactory power, or p.ol (the negative log of the molar concentration of the odorant in air at which a human first detects the presence of the odorant). These values can be directly transposed to other commonly used units such as ppm (volume) and ppb (volume): thresholds of 1 ppm and 1 ppb are equivalent to p.ol=6 and p.ol=9, respectively. Odor Detection Threshold can be measured, for example, by the method in International Publication Number WO 2006/138726.

"Cyclodextrin complex" refers to a complex of cyclodextrin and perfume.

"Molecular weight," unless otherwise designated, refers to the weight average molecular weight which can be calculated by using the sum of the molecular weights of the elements in a molecule. These can be found, for example, in *Atomic Weights of the Elements*, Weiser, 2005.

"Room temperature as used herein refers to about 20° C.

"Personal aerosol composition" refers to a composition for application to the skin or clothing for purposes of personal hygiene and/or perfume application, for example.

Many consumers enjoy a good scent in a consumer product. Scent can be delivered through a multitude of means, like direct addition of a scent to a product or through the use of a scent delivery agent. Scent delivery agents can enhance and/or change the delivery of the scent. For example, some delivery agents can encapsulate a perfume so that it can be released upon a triggering event. Other delivery agents can help a perfume deposit onto a target surface so that the perfume is more easily detected by the consumer.

Perfumes are usually not a single component, but made up of multiple perfume raw materials which combined give the overall scent of the perfume. Each of the perfume raw materials has its own characteristic and its own chemical properties, like molecular weight, c Log P, etc. These properties can influence where and how long a scent can be detected. Some of these properties are how perfume raw materials are divided into top, middle, and base notes.

Previously, when using a perfume in combination with a delivery agent like a cyclodextrin, it was believed that most of the perfume was released from the delivery agent upon the triggering event. For cyclodextrins, the triggering event is usually the introduction of moisture. However, it was recently discovered that only about 4%, of a complexed perfume, was being released from a "high" performing cyclodextrin perfume complex upon exposure to moisture. Thus, surprisingly, most of the perfume was remaining within the cyclodextrin and was not noticeable to the consumer. This means there is significant room for improvement in the efficacy of cyclodextrin perfume complexes.

Figure 3:
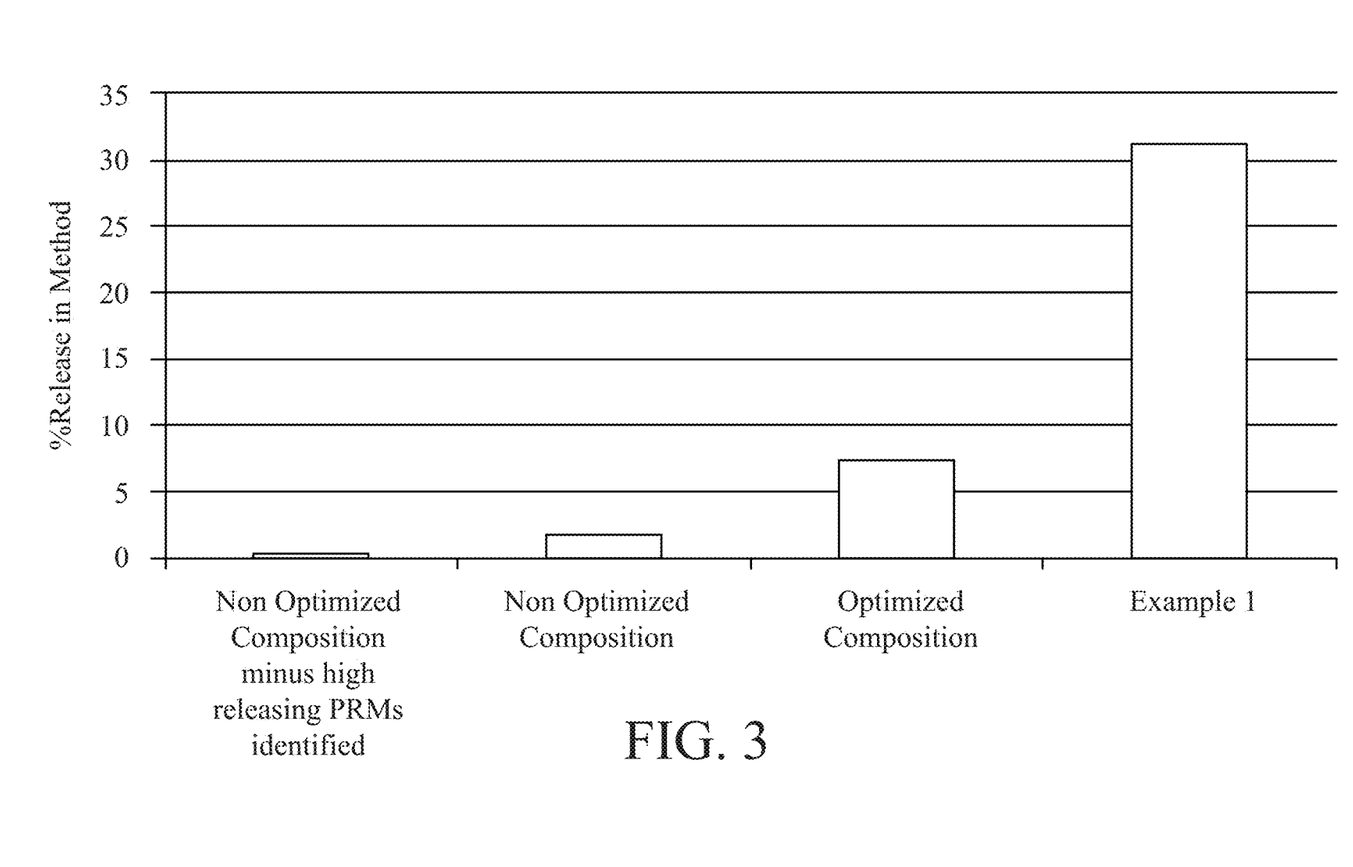
FIG. 3 is a graph showing the percentage of perfume complexed with a beta cyclodextrin that is released when measured in accordance with the In Vitro Perfume Release Method.

An understanding of what is and what isn't releasing from a cyclodextrin was thought helpful to improve the efficacy of the perfume cyclodextrin complex. Since less than 5% of the perfume compositions used in a cyclodextrin complex were efficiently releasing from the cyclodextrin complex (see FIG. 3, Non Optimized Composition), the perfume raw materials that were being release from the cyclodextrins were identified to determine if there were characteristics common among them which could be used to help develop a perfume composition for optimized released from a cyclodextrin.

With water being the key releasing agent, it was found that perfume materials with more affinity with water (lower log P) had better release from the cyclodextrin complex. Perfume materials with a lower cyclodextrin complex stability constant (log k) also had better release from a cyclodextrin complex. In addition, a lower molecular weight, which may correlate with a lower cyclodextrin complex stability constant, also correlates with a better release. To demonstrate these characteristics as impacting the release from the cyclodextrin composition, new perfume compositions were created. One composition removed these higher releasing perfume materials from the original low release composition as a negative control check (see FIG. 3, Non Optimized Composition minus high releasing PRM's identified vs. Non Optimized Composition). These compositions were then complexed with a beta cyclodextrin and tested for release. In release testing, the Non Optimized Composition minus the high releasing PRM's had less than one third of the release of the original Non Optimized Composition (see FIG. 3). This helped confirm which materials were releasing from the cyclodextrin complex.

An optimized composition was also made which utilized about 70%, by weight of the perfume composition, of perfume raw materials with a log P, stability constant, and weight average molecular weight believed to help with perfume release from a cyclodextrin complex. This perfume, Optimized Composition from FIG. 3, had 4 times the release of the original composition (Non Optimized Composition). Another perfume composition was made with 100% of the perfume composition matching these physical property characteristics (Example 1). This perfume composition had over 15 times the release of the Non Optimized Composition.

Figure 1:
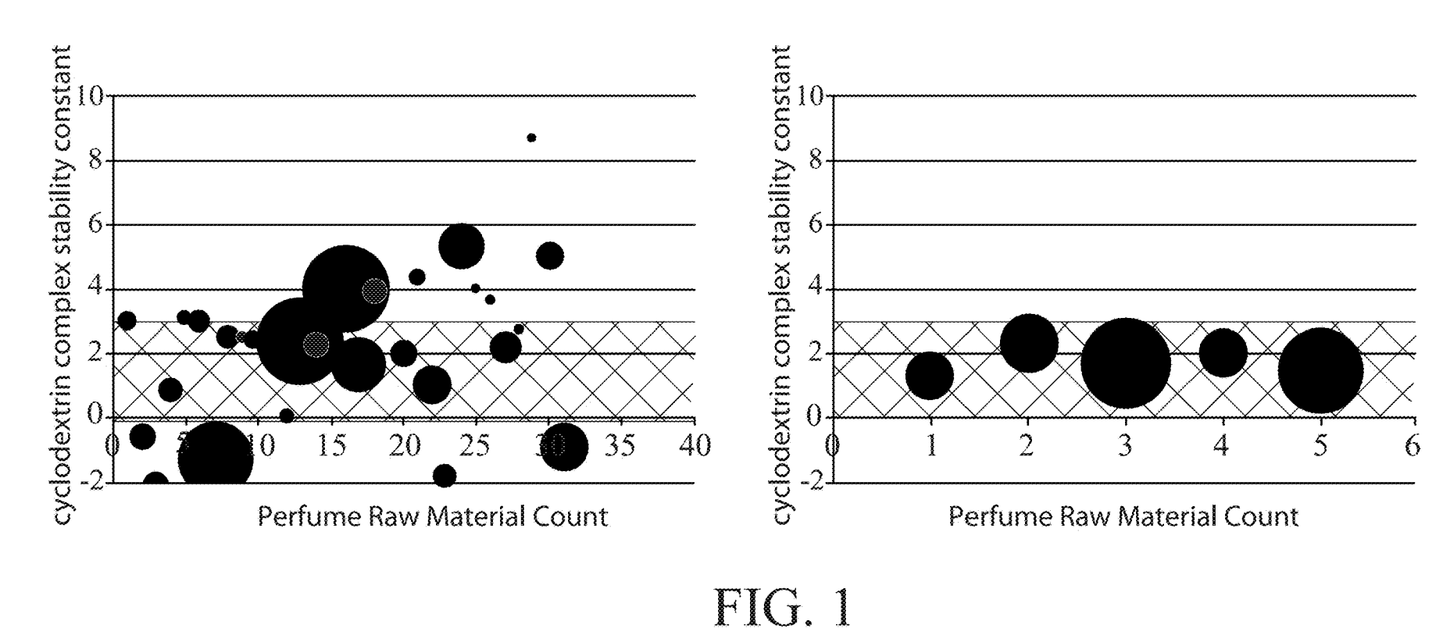
FIG. 1 is a side-by-side comparison of the cyclodextrin complex stability constant (BCD binding strength) of a perfume composition before and after optimization for release from a cyclodextrin complex.

As noted above, one of the characteristics of a perfume raw material that can impact its release from a cyclodextrin is its complex stability constant. This signifies how strongly the perfume raw material binds with the cyclodextrin. While a minimum complex stability constant allows for a perfume raw material to bind and stay bound, at some point the affinity of the perfume raw material for the cyclodextrin can become so strong that it becomes difficult to release. It is believed that a complex stability constant of more than 3 can interfere with the release of the perfume raw material upon a triggering event. This is not to say that perfume raw materials with a complex stability constant above a 3 cannot be used, just that the ability to release such materials should be taken into consideration during perfume design. For example, FIG. 1 shows the binding complex of perfume raw materials in a perfume composition. The graph on the left shows the make-up of a more typical perfume, while the graph on the right shows a perfume composition after optimization for release from a cyclodextrin. The optimized formula showed an improvement of more than 15 times over Non Optimized Perfume A.

Figure 2:
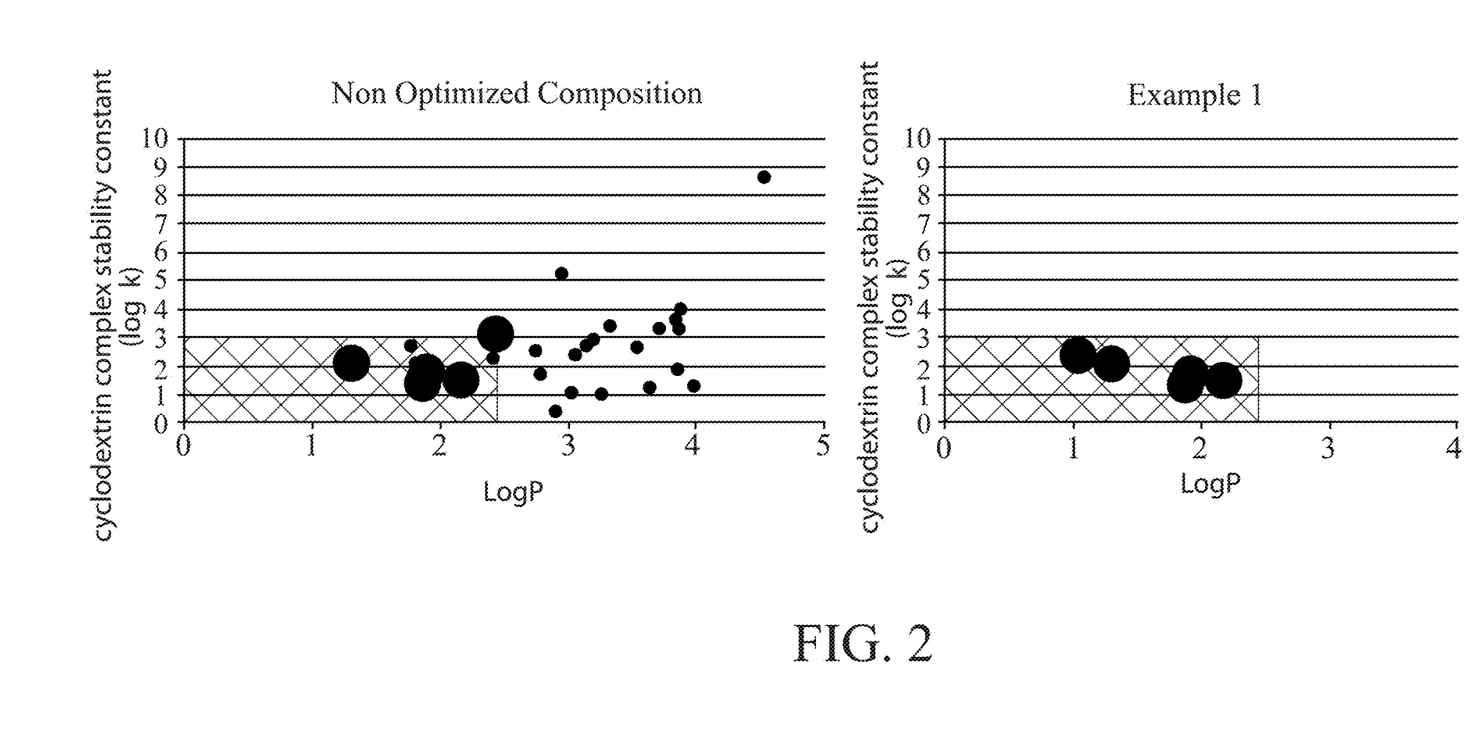
FIG. 2 is a side-by-side comparison of the cyclodextrin complex stability constant over Log P of a perfume composition before and after optimization for release from a cyclodextrin complex.

Another property of a perfume raw material which can impact its ability to release from a cyclodextrin is its C log P. C log P is the calculation of the log P value of a compound, which is the logarithm of its partition coefficient between n-octanol and water ($C_{octanol}/C_{water}$). Thus log P, or if calculated, c Log P, is a measure of a perfume raw material's hydrophilicity. High log P values correspond to low hydrophilicities. It is believed that a low log P, i.e. higher affinity for water, can positively impact the release of a perfume raw material from a cyclodextrin upon appropriate contact with moisture. For example, FIG. 2 shows the binding complex of perfume raw materials in a perfume and the C log P. The graph on the left shows the make-up of a more typical perfume, while the graph on the right shows a perfume composition after optimization for release from a cyclodextrin. The optimized formula complexed with a beta cyclodextrin showed an improvement of 15 times over the Non Optimized Composition. For this application, it is believed a C log P value of about 2.5 or less is optimal for release from a cyclodextrin complex.

A third property that can impact the release of a perfume raw material from a cyclodextrin is its weight average molecular weight. It is believed that perfume raw materials which are smaller in size will have less binding points to a cyclodextrin and thus more easily released. Ideally, a perfume raw material for optimal release will have a weight average molecular weight of about 200 Daltons or less.

A fourth property that can impact the need for efficacy is the odor detection threshold. Odor detection threshold is the minimum level at which a perfume raw material can be detected by the average human nose. For a perfume raw material with a low odor detection threshold, less of the perfume raw material needs to be released from a cyclodextrin in order for the perfume raw material to be noticed. This feature can allow for the use of perfume raw materials which would otherwise be seen as too difficult to release en masse from a cyclodextrin as only a small amount of release can be noticeable to a consumer. Optimally, the odor detection threshold of a perfume raw material is about 7–log molar concentration or more.

Figure 4:
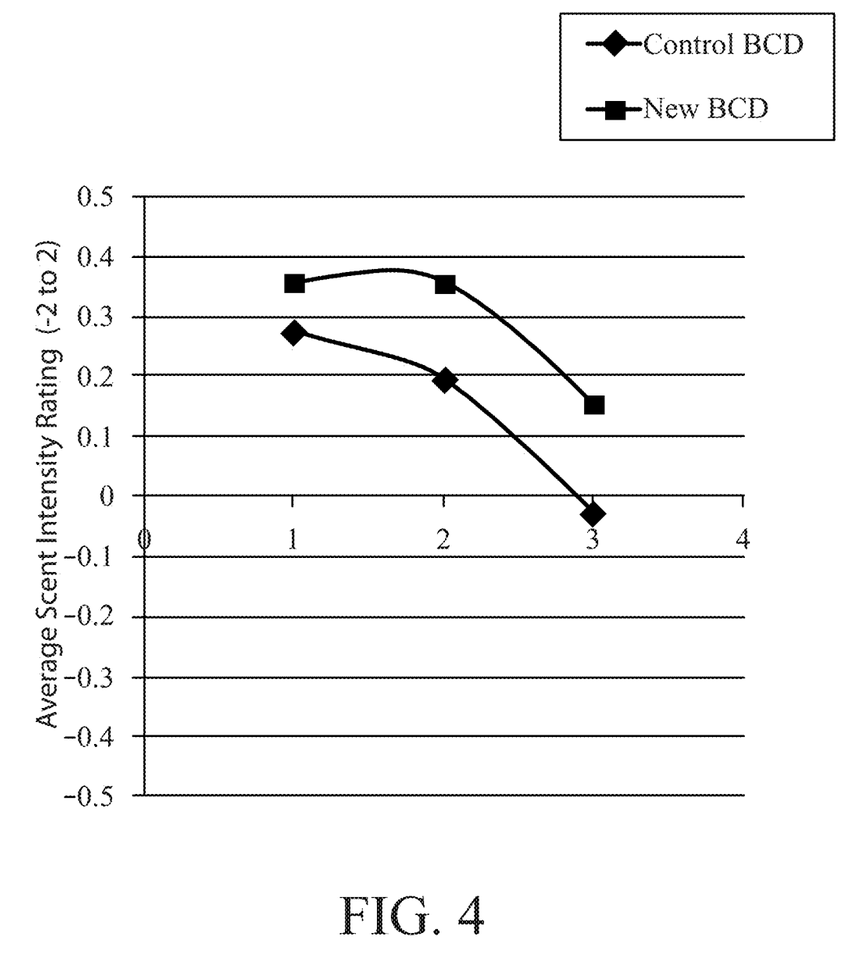
FIG. 4 is a graph showing the average scent intensity at each assessment time point, where 1 is at application, 2 is during the day, and 3 is at the end of the day.

To determine whether the release enhancement was noticeable to consumers, an optimized beta cyclodextrin perfume complex was placed into an invisible solid antiperspirant product and was tested against an in market beta cyclodextrin complex with less than 5% release in a similar product. The products were given to over 90 consumers each to wear every day for 2 weeks. After the 2 weeks they were asked to rate the intensity of the perfume on a scale of −2 (much too weak) to 2 (much too strong). They rated the product they wore at application, during the day, and at the end of the day. FIG. 4 shows on average those who wore the product with the optimized cyclodextrin reported a higher perfume intensity at each time point evaluated. With the single variable change of the perfume in the cyclodextrin perfume complex between the two test products, we believe the increase in fragrance intensity can be attributed to the optimized perfume in the cyclodextrin perfume complex.

Personal Aerosol Composition

A personal aerosol composition comprises a solvent, a cyclodextrin perfume complex, and a propellant. The cyclodextrin perfume complex comprises a cyclodextrin and a perfume. The composition can include from about 10% to about 80%, by weight of the composition, of solvent. The composition can include from about 0.1% to about 25%, by weight of the composition, of a cyclodextrin perfume complex. The composition can include from about 20% to about 95%, by weight of the composition, of propellant.

Solvent

A personal aerosol composition comprises a solvent. The solvent can be volatile, non-volatile, or a combination thereof. The composition can include from about 10% to about 80%, by weight of the composition, of solvent. In addition, the composition can comprise from about 10%, from about 15%, from about 20%, to about 50%, to about 60%, to about 70%, to about 80%, or any combination thereof, by weight of the composition, of solvent.

Volatile Solvents

The compositions described herein may include a volatile solvent or a mixture of volatile solvents. The volatile solvents may comprise from about 2%, from about 5%, from about 8%, from about 10%, from about 15%, from about 20%, to about 20%, to about 25%, to about 30%, to about 35%, to about 40%, to about 50%, about 60%, about 70%, about 80%, or any combination thereof, by weight of the composition, of volatile solvent. The volatile solvents useful herein may be relatively odorless and safe for use on human skin. Suitable volatile solvents may include $C_1$-$C_4$ alcohols and mixtures thereof. For example, ethanol may be used as the volatile solvent. Some other non-limiting examples of volatile solvents include methanol, propanol, isopropanol, butanol, and mixtures thereof.

Nonvolatile Solvents

The composition may comprise from about 2%, from about 5%, from about 8%, from about 10%, from about 15%, from about 20%, to about 20%, to about 25%, to about 30%, to about 35%, to about 40%, to about 50%, to about 60%, to about 70%, to about 80%, or any combination thereof, by weight of the composition, of nonvolatile solvent. The composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof. If present, the nonvolatile solvent may be included at a weight ratio of the nonvolatile solvent to the cyclodextrin complex of less than 1:1, less than 1:2, less than 1:10, or less than 1:100. The nonvolatile solvent may also be included at a weight ratio of the nonvolatile solvent to the cyclodextrin perfume complex of less than about 1:1, less than about 1:2, less than about 1:10, or less than about 1:100, but greater than 0. The composition may also be free of nonvolatile solvents.

Cyclodextrin Perfume Complex

The composition can comprise a cyclodextrin perfume complex. The composition can comprise from about 0.1%, from about 1%, from about 2%, or from about 3%; to about 25%, to about 20%, to about 15% or to about 10%, by weight of the composition, of a cyclodextrin perfume complex.

Cyclodextrin

A cyclodextrin may be used for substantially "hiding" a perfume material until a triggering mechanism has occurred, such as, for example, perspiration, urination, or menstruation, to "release" the perfume material. As used herein, the term "cyclodextrin" includes any of the known cyclodextrins such as unsubstituted cyclodextrins containing from about six to about twelve glucose units, especially alpha-cyclodextrin, beta-cyclodextrin, gamma-cyclodextrin, and/or mixtures thereof. For example, cyclodextrins may be selected from the group consisting of beta-cyclodextrin, hydroxypropyl alpha-cyclodextrin, hydroxypropyl beta-cyclodextrin, methylated-alpha-cyclodextrin, methylated-beta-cyclodextrin, and mixtures thereof.

Cyclodextrin particles and cyclodextrin complexes comprising a perfume can be formed by various methods. For example, a solvent (e.g., water), unloaded cyclodextrin particles, and a perfume material can be placed into a container and then mixed for a period of time to permit loading of perfume molecules into "cavities" of cyclodextrin molecules. The mixture may or may not be processed further; e.g., processed through a colloid mill and/or homogenizer. The solvent is then substantially removed, like by drying, from the resulting mixture or slurry to yield cyclodextrin complex particles. Different manufacturing techniques may however impart different particle/complex characterizations, which may or may not be desirable in the product.

The particles and/or complexes can have a low level of moisture prior to their inclusion into a product. For example, some may have a moisture level of less than about 20% by weight of the particles, less than about 10% by weight of the particles, or even less than about 6% by weight of the particles, to about 0%, prior to the inclusion of the volume of particles or complexes into a composition. Other moisture levels may also be suitable.

Spray drying a slurry or mixture of cyclodextrin-perfume complexes is one manufacturing technique capable of producing the cyclodextrin particles and cyclodextrin complexes having the above-noted, low moisture levels. Table 1 below provides a comparison of spray dried cyclodextrin complexes versus complexes formed via an extruder process (kneading).

TABLE I

| Cyclodextrin Complex Moisture Level | |
|---|---|
| Sample | % Moisture |
| Spray Dry Process Sample A | 4.4 |
| Spray Dry Process Sample B | 3.7-4.5 |
| Spray Dry Process Sample C | 5.3 |
| Extruder Process Sample A | 27.87 |
| Extruder Process Sample B | 27.97 |
| Extruder Process Sample C | 24.00 |

Water content, USP (United States Pharmacopeia, current as of Aug. 1, 2006)<921> Method I is the analytical method for determining cyclodextrin complex moisture level, as shown in Table I.

As one can see from Table 1, the moisture level directly manifested by these two methods is dramatically different. It should be understood that this comparison is not intended to disclaim kneading/extruder processes from appended claims that do not specify a particular complex formation process. Rather, a kneading and extrusion method, or other method forming particles/complexes with higher than desired moisture levels, could utilize additional processing after their initial formation. For example, extruded complexes may be processed through an oven or dryer, or exposed to a controlled environment for a period of time.

Although not wishing to be bound by theory, it is believed that cyclodextrin particles/complexes having a relatively high moisture level have an increased tendency to agglomerate. The agglomerated particles may reach a size so as to become perceptible by a consumer; that is, a consumer may characterize the composition as being "gritty." A "gritty" composition may not be desirable to some consumers. Microbial growth is another potential disadvantage associated with employing cyclodextrin particles/complexes with relatively high moisture levels into a final composition depending on the remaining ingredients of the composition and/or storage parameters.

The efficiency or level of complexing with a perfume material is another parameter of cyclodextrin complexes that can vary greatly depending on the manufacturing techniques employed. Put another way, the percent of perfume material that is associated with the interior of a cyclodextrin molecule compared to the percent of perfume material that is associated with the exterior of the cyclodextrin complex. The perfume material that is on the exterior region of the complex is essentially free to be expressed without the requirement of a triggering mechanism. The probability that a consumer perceives the perfume material prior to a triggering mechanism increases as the level of free perfume increases. And perception of a perfume material prior to a triggering mechanism may not be desired depending on the overall composition design and targeted benefit associated with employment of the cyclodextrin complexes. The percent of perfume material that is complexed with cyclodextrin can be, for example, greater than about 75%, in some instances greater than about 90%, and in other instances greater than about 95%. It should be understood that these levels of perfume complexation are directly associated with the complex formation process itself; the percentages do not represent a formulation design of adding a first percentage of perfume material via a cyclodextrin complex and adding a second percentage of neat perfume material.

Spray drying a slurry or mixture of cyclodextrin-perfume complexes is one manufacturing technique capable of producing cyclodextrin complexes having the above-noted levels of perfume complexation. Table II below provides a comparison of spray dried cyclodextrin complexes versus complexes formed via an extruder process (kneading).

TABLE II

Percent of Perfume Loading in Cyclodextrin Complexes

| Sample | Complexation Efficiency |
|---|---|
| Spray Dry Process Sample A | 96.6 |
| Spray Dry Process Sample B | 96.8 |
| Spray Dry Process Sample C | 96.2 |
| Extruder Process Sample A | 60.77 |
| Extruder Process Sample B | 65.47 |
| Extruder Process Sample C | 67.07 |

One can see from Table II that spray drying is capable of producing cyclodextrin complexes with very little free perfume as compared to a kneading/extruder process. The skilled artisan should appreciate that the comparison provided in Table II is not intended to disclaim kneading/extruder processes from appended claims that do not specify a particular complex formation process. Rather, additional processing steps may, for example, be employed to eliminate free perfume associated with extruded complexes prior to their inclusion into a composition.

The analytical method for determining the percent of perfume complexed, as shown in Table II, determines the free perfume level in the complex by dissolving a sample in tetrahydrofuran (THF) adding an internal standard, and analyzing by capillary gas chromatography (GC). The complexed perfume level is measured by extracting the same sample in acetone containing an internal standard, and analyzing by GC.

Complexation Efficiency=% Complexed/[% Complexed+% Free]

Perfume Compositions

A perfume composition comprises perfume raw materials. At least a portion of the perfume raw materials may have a complex stability constant of about 3.0 or less; about 2.5 or less, about 2.0 or less, about 1.0 or less, to about 0, to about −1, to about −2, or any combination thereof. Some of the perfume raw material may have a c Log P of about 2.5 or less, about 2.0 or less, about 1.5 or less, about 1.0 or less, to about −3. Some of the perfume raw materials may have a weight average molecular weight of about 200 Daltons or less, about 180 Daltons or less, about 150 Daltons or less, about 100 Daltons or less, to about 50 Daltons. A perfume raw material will have an odor detection threshold. At least a portion of the perfume raw materials in a perfume composition will have an odor detection threshold of about 7−log molar concentration or greater; about 8−log molar concentration or greater; about 9−log molar concentration or greater; to about 11.5−log molar concentration.

The perfume composition comprises about 10% or more, by weight of the perfume, of perfume raw materials which have a complex stability constant of about 3.0 or less, a c Log P of about 2.5 or less, and a weight average molecular weight of about 200 Daltons or less. Going further, the perfume composition may comprise about 20% or more; about 30% or more; about 40% or more, or about 50% or more, up to 100%; of perfume raw materials which have a complex stability constant of about 3.0 or less, a c Log P of about 2.5 or less, and a weight average molecular weight of about 200 Daltons or less. In addition, a perfume composition may also include perfume raw materials with an odor detection threshold of about 7−log molar concentration.

A representative, non-limiting, list of perfume raw materials that have a complex stability constant of about 3.0 or less, a c Log P of about 2.5 or less, and a weight average molecular weight of about 200 Daltons or less is included in the chart below.

| CAS Number | Name | LogP (v3.0) | Formula Weight | Odor Detection Threshold, Neural Net model | bCD Complex Stability Constant |
|---|---|---|---|---|---|
| 10031-96-6 | eugenyl formate | 2.35 | 192.21 | 8.84 | 2.71 |
| 100-52-7 | Benzaldehyde | 1.4 | 106.12 | 7.45 | 2.19 |
| 10094-40-3 | 2-hexen-1-yl acetate | 2.21 | 142.20 | 8.20 | 1.45 |
| 101-39-3 | alpha-methyl cinnamaldehyde | 2.18 | 146.19 | 8.83 | 1.08 |
| 101-41-7 | Methyl phenylacetate | 1.89 | 150.18 | 8.02 | 2.14 |
| 101-48-4 | Viridine (PADMA) | 1.65 | 166.22 | 8.01 | 2.26 |
| 101-97-3 | Ethyl 2-phenylacetate | 2.39 | 164.20 | 8.63 | 2.25 |
| 103-25-3 | methyl hydrocinnamate | 2.04 | 164.20 | 8.20 | 2.24 |
| 103-26-4 | Methyl cinnamate | 2.44 | 162.19 | 8.97 | 2.07 |
| 103-45-7 | 2-Phenylethyl acetate | 2.07 | 164.20 | 8.15 | 1.54 |
| 103-54-8 | Cinnamyl acetate | 2.49 | 176.22 | 8.51 | 1.53 |
| 104-09-6 | lilac acetaldehyde | 2.12 | 134.18 | 9.36 | 2.67 |
| 104-20-1 | 4-(p-Methoxyphenyl)-2-butanone (frambinone) | 1.88 | 178.23 | 8.86 | 1.72 |
| 104-46-1 | Anethole | 2.43 | 148.20 | 8.79 | 2.34 |
| 104-50-7 | gamma-Octalactone | 2.06 | 142.20 | 8.30 | 2.94 |
| 104-53-0 | 3-phenyl propionaldehyde | 1.65 | 134.18 | 8.95 | 2.47 |
| 104-54-1 | Cinnamic alcohol | 1.68 | 134.18 | 8.58 | 2.15 |
| 104-55-2 | Cinnamic aldehyde | 1.92 | 132.16 | 8.56 | 2.37 |
| 104-62-1 | Phenethyl formate | 1.82 | 150.18 | 8.10 | 2.32 |
| 104-64-3 | 3-phenyl propyl formate | 2.22 | 164.20 | 8.51 | 2.46 |
| 105-01-1 | Isobutyl furylpropionate | 2.34 | 196.25 | 8.60 | 2.30 |
| 10521-96-7 | Styryl acetate | 2.3 | 162.19 | 8.60 | 1.47 |
| 105-86-2 | geranyl formate | 2.44 | 182.26 | 8.49 | −1.85 |
| 10606-47-0 | 3-Hepten-1-ol | 1.79 | 114.19 | 8.47 | 2.11 |
| 106-22-9 | Citronellol | 2.49 | 156.27 | 8.37 | −0.64 |
| 106-24-1 | trans-Geraniol | 1.95 | 154.25 | 9.36 | −2.13 |
| 106-25-2 | Nerol | 1.95 | 154.25 | 9.36 | −2.13 |
| 106-26-3 | Neral | 2.33 | 152.24 | 8.48 | −1.82 |
| 106-72-9 | melon heptenal (melonal) | 2.09 | 140.23 | 8.09 | −0.64 |
| 107-03-9 | Propyl mercaptan | 1.87 | 76.16 | 9.04 | 0.65 |
| 1073-26-3 | 2-Propionylpyrrole | 1.37 | 123.15 | 8.13 | 1.88 |
| 110458-85-0 | 5,6-Dimethyl-1-(1-methylethenyl) bicyclo[2.2.1]hept-5-ene-2-methanol | 2.36 | 192.30 | 9.46 | 1.27 |
| 1123-85-9 | Hydratopic alcohol | 1.85 | 136.19 | 8.19 | 1.99 |
| 1131-62-0 | 3,4-Dimethoxyacetophenone | 1.7 | 180.20 | 8.15 | 1.63 |
| 116-26-7 | Safranal | 2.4 | 150.22 | 8.54 | 1.30 |
| 118-93-4 | 2-Hydroxyacetophenone | 1.97 | 136.15 | 8.15 | 1.38 |
| 1197-06-4 | cis-carveol | 1.86 | 152.24 | 8.60 | 0.32 |
| 1205-17-0 | ocean propanal (helional) | 1.77 | 192.21 | 8.89 | 2.67 |
| 120-58-1 | Isosafrol | 2.01 | 162.19 | 8.45 | 2.52 |
| 120-72-9 | Indole | 2.34 | 117.15 | 8.20 | 2.19 |
| 120-75-2 | 2-Methylbenzothiazole | 2.14 | 149.21 | 8.12 | 2.83 |
| 121-32-4 | Ethyl vanillin | 1.53 | 166.18 | 10.32 | 2.41 |
| 121-33-5 | Vanillin | 1.04 | 152.15 | 9.93 | 2.36 |
| 121-98-2 | Methyl p-anisate | 1.99 | 166.18 | 8.54 | 2.05 |
| 122-63-4 | Benzyl propionate | 2.24 | 164.20 | 8.29 | 2.01 |
| 122-72-5 | 3-phenyl propyl acetate | 2.48 | 178.23 | 8.70 | 1.73 |
| 122-78-1 | phenyl acetaldehyde | 1.46 | 120.15 | 8.40 | 2.30 |
| 123-08-0 | p-Hydroxybenzaldehyde | 1.29 | 122.12 | 9.34 | 2.28 |
| 123-11-5 | para-anisaldehyde | 1.53 | 136.15 | 7.72 | 2.29 |
| 123-92-2 | Isoamyl acetate | 1.87 | 130.19 | 7.12 | 1.33 |
| 13327-56-5 | Ethyl 3-methylthiopropionate | 1.47 | 148.22 | 8.09 | 1.88 |
| 134-20-3 | Methyl anthranilate | 1.58 | 151.17 | 8.22 | 1.69 |
| 13494-08-1 | 1,2-Cyclopentanedione, 3-ethyl- | 0.5 | 126.16 | 8.29 | 2.72 |
| 134-96-3 | Syringaldehyde | 0.94 | 182.18 | 9.89 | 2.48 |
| 13678-68-7 | furfuryl thioacetate | 1.09 | 156.20 | 8.11 | 1.33 |
| 13679-85-1 | blackberry thiophenone | 0.73 | 116.18 | 8.44 | 2.06 |
| 140-39-6 | p-Cresyl acetate | 2.17 | 150.18 | 8.10 | 1.67 |
| 14049-11-7 | linalool oxide (pyranoid) | 1.89 | 170.25 | 8.45 | 2.62 |
| 141-27-5 | Geranial | 2.33 | 152.24 | 8.48 | −1.82 |
| 142653-61-0 | Parmanyl | 1.75 | 153.22 | 8.13 | 2.05 |
| 142-83-6 | Sorbinaldehyde | 1.29 | 96.13 | 8.57 | 2.29 |
| 14360-50-0 | Pentyl 2-furyl ketone | 2.49 | 166.22 | 9.39 | 2.44 |
| 150-19-6 | m-Guaiacol | 1.39 | 124.14 | 8.16 | 2.02 |
| 1504-55-8 | alpha-Methylcinnamic alcohol (cypriol) | 1.73 | 148.20 | 8.68 | 0.74 |
| 15111-56-5 | Ethyl cyclohex-3-enecarboxylate | 1.86 | 154.21 | 8.47 | 2.78 |
| 1516-17-2 | 2,4-Hexadienyl acetate | 1.75 | 110.16 | 8.30 | 1.36 |
| 15174-69-3 | 4-Hydroxy-3-methylbenzaldehyde | 1.63 | 136.15 | 10.25 | 2.24 |
| 15186-51-3 | Furan, 3-methyl-2-(3-methyl-2-butenyl)- | 2.04 | 150.22 | 8.26 | −0.46 |
| 1540-28-9 | n-Pentyl acetoacetate | 1.63 | 172.22 | 8.04 | 1.79 |
| 1552-67-6 | Ethyl 2-hexenoate | 2.49 | 142.20 | 8.30 | 2.12 |
| 15679-12-6 | 2-Ethyl-4-methylthiazole | 1.69 | 127.20 | 8.31 | 2.13 |
| 15679-13-7 | tropical thiazole | 2.12 | 141.23 | 8.25 | 2.33 |

-continued

| CAS Number | Name | LogP (v3.0) | Formula Weight | Odor Detection Threshold, Neural Net model | bCD Complex Stability Constant |
|---|---|---|---|---|---|
| 16251-77-7 | Trifernal | 2.28 | 148.20 | 8.87 | 2.51 |
| 1646-26-0 | Coumarone | 1.9 | 160.17 | 8.64 | 1.90 |
| 16491-25-1 | 2,4-Hexadienyl propionate | 2.44 | 154.21 | 8.72 | 1.97 |
| 1679-07-8 | Cyclopentyl mercaptan | 2.24 | 102.19 | 9.09 | 1.47 |
| 1679-09-0 | 2-Methyl-2-butanethiol | 2.45 | 104.21 | 9.16 | 0.79 |
| 16957-70-3 | trans-2-Methyl-2-pentenoic acid (Strawberriff) | 1.33 | 114.14 | 8.78 | 0.65 |
| 1708-34-5 | 2-Hexyl-1,3-dioxolane | 2.17 | 158.24 | 8.11 | 2.56 |
| 1708-81-2 | cis-3-Hepten-1-ol | 1.79 | 114.19 | 8.47 | 2.11 |
| 1708-82-3 | 3-Hexenyl acetate | 2.18 | 142.20 | 8.16 | 1.48 |
| 17102-64-6 | Trans,trans-2,4-Hexadien-1-01 | 0.96 | 98.14 | 8.22 | 2.06 |
| 1754-62-7 | Methyl Trans-Cinnamate, 99% | 2.44 | 162.19 | 8.97 | 2.07 |
| 1759-28-0 | 4-Methyl-5-vinylthiazole | 1.51 | 125.19 | 8.56 | 1.62 |
| 17626-75-4 | 2-Propylthiazole | 1.51 | 127.20 | 8.23 | 1.79 |
| 18031-40-8 | (S),(-)-Perillaaldehyde | 2.34 | 150.22 | 9.80 | 1.85 |
| 18277-27-5 | 2-(1-Methylpropyl)thiazole | 1.9 | 141.23 | 8.25 | 1.71 |
| 18479-68-0 | (+)-P-Menth-1-en-9-ol, 97%, mixture of isomers | 2.26 | 154.25 | 8.87 | 1.66 |
| 18640-74-9 | Isobutyl thiazole | 1.92 | 141.23 | 8.29 | 2.02 |
| 18829-55-5 | trans-2-Heptenal | 2.1 | 112.17 | 8.76 | 2.33 |
| 18881-04-4 | (1S)-(−)-cis-Verbenol | 2.03 | 152.24 | 8.09 | 2.61 |
| 189440-77-5 | Anapear | 2.3 | 154.21 | 8.78 | 2.20 |
| 1901-38-8 | alpha-Campholenic alcohol | 2.03 | 154.25 | 8.08 | 1.32 |
| 19788-49-9 | Ethyl 2-mercaptopropionate | 1.41 | 134.19 | 8.39 | 0.99 |
| 19819-98-8 | 2-Methylphenethyl alcohol | 1.66 | 136.19 | 8.46 | 2.36 |
| 2046-17-5 | Methyl 4-phenylbutyrate | 2.46 | 178.23 | 8.75 | 2.37 |
| 20474-93-5 | Allyl crotonate | 1.63 | 126.16 | 8.29 | 2.24 |
| 2051-78-7 | Allyl butyrate | 1.88 | 128.17 | 8.17 | 2.21 |
| 2051-96-9 | Benzyl lactate | 1.35 | 180.20 | 8.15 | 1.70 |
| 20665-85-4 | Vanillin isobutyrate | 1.92 | 222.24 | 8.20 | 2.20 |
| 2111-75-3 | perillaldehyde | 2.34 | 150.22 | 9.80 | 1.85 |
| 2142-94-1 | Neryl Formate | 2.44 | 182.26 | 8.49 | −1.85 |
| 2179-58-0 | Allyl methyl disulfide | 1.9 | 120.23 | 8.59 | 1.44 |
| 2179-60-4 | Methyl propyl disulfide | 2.28 | 122.24 | 8.56 | 1.97 |
| 21835-00-7 | 2-Cyclopenten-1-one, 2-hydroxy-3,4-dimethyl- | −0.02 | 126.16 | 8.91 | 0.76 |
| 21835-01-8 | 3-Ethyl-2-hydroxy-2-cyclopenten-1-one | 0.06 | 126.16 | 8.79 | 2.41 |
| 22104-78-5 | 2-Octenol-1 | 2.27 | 128.21 | 8.81 | 2.24 |
| 2217-33-6 | Tetrahydrofurfuryl butyrate | 1.54 | 172.22 | 8.40 | 2.22 |
| 22451-63-4 | Allo-ocimenol | 2.42 | 152.24 | 8.51 | −0.99 |
| 22460-95-3 | 7-Octene-1,6-diol, 3,7-dimethyl- | 1.33 | 172.27 | 8.27 | 0.79 |
| 22924-15-8 | 3-Ethoxybenzaldehyde | 1.99 | 150.18 | 8.14 | 2.33 |
| 22927-13-5 | 2-Ethylbenzaldehyde | 2.06 | 134.18 | 8.78 | 2.53 |
| 2305-21-7 | 2-hexen-1-ol | 1.3 | 100.16 | 8.09 | 2.06 |
| 23495-12-7 | Phenoxyethyl propionate | 2.43 | 194.23 | 8.92 | 1.78 |
| 23911-56-0 | Nerolione | 2.02 | 174.20 | 8.74 | 2.04 |
| 2445-83-2 | 7-Methylcoumarin | 2.42 | 160.17 | 8.79 | 2.78 |
| 2463-63-0 | Butylacrolein | 2.1 | 112.17 | 8.76 | 2.33 |
| 2497-18-9 | 2-Hexen-1-yl acetate | 2.21 | 142.20 | 8.20 | 1.45 |
| 2555-49-9 | Ethyl phenoxyacetate | 2.04 | 180.20 | 8.36 | 1.93 |
| 26553-46-8 | Ethyl trans-3-hexenoate | 2.25 | 142.20 | 8.34 | 2.14 |
| 8/6/2719 | N-Acetyl methyl anthranilate | 1.21 | 193.20 | 8.00 | 1.48 |
| 27829-72-7 | Ethyl trans-2-hexenoate | 2.49 | 142.20 | 8.30 | 2.12 |
| 27939-60-2 | Vertoliff (triplal extra) | 1.8 | 138.21 | 9.24 | 1.71 |
| 28069-72-9 | (2E,6Z)-Nona-2,6-dien-1-ol | 2.43 | 140.23 | 9.59 | 2.24 |
| 28977-58-4 | Ocimenol | 2.02 | 152.24 | 8.71 | −0.59 |
| 29414-56-0 | 2,6-Dimethyl-1,5,7-octatrienol-3 | 1.96 | 152.24 | 8.89 | −0.76 |
| 29548-14-9 | p-Menth-1-ene-9-al | 2.24 | 152.24 | 9.40 | 1.85 |
| 30361-28-5 | 2,4-Octadien-1-al | 2.45 | 124.18 | 9.33 | 2.32 |
| 30954-98-4 | Propyl anthranilate | 2.47 | 179.22 | 8.88 | 1.87 |
| 3194-17-0 | 2-Pentanoylfuran | 1.99 | 152.19 | 8.97 | 2.40 |
| 32272-48-3 | 4-Ethyl-2-methylthiazole | 1.7 | 127.20 | 8.32 | 2.25 |
| 32764-98-0 | Jasmolactone | 2.36 | 168.24 | 8.72 | 2.96 |
| 33467-73-1 | cis-3-Hexenyl formate | 1.69 | 128.17 | 8.22 | 2.25 |
| 3391-86-4 | 1-Octenol-3 | 2.36 | 128.21 | 8.29 | 2.19 |
| 3581-91-7 | 4,5-Dimethylthiazole | 0.91 | 113.18 | 8.10 | 1.30 |
| 3583-00-4 | 4,4-Dimethyl-5-isopropyl-1,3-dioxolane | 1.92 | 158.24 | 8.99 | 1.98 |
| 35926-04-6 | 1-Hexen-3-yl acetate | 2.31 | 142.20 | 8.02 | 1.68 |
| 36701-01-6 | Furfuryl valerate | 1.89 | 182.22 | 8.39 | 2.12 |
| 36806-46-9 | 2,6-Dimethyl-6-hepten-1-ol | 2.4 | 142.24 | 8.07 | 0.76 |
| 3681-71-8 | cis-3-Hexenyl acetate | 2.18 | 142.20 | 8.16 | 1.48 |
| 3681-82-1 | trans-3-Hexenyl acetate | 2.18 | 142.20 | 8.16 | 1.48 |
| 36880-33-8 | 5-Ethyl-2-thiophenecarbaldehyde | 1.85 | 140.20 | 8.19 | 2.64 |

-continued

| CAS Number | Name | LogP (v3.0) | Formula Weight | Odor Detection Threshold, Neural Net model | bCD Complex Stability Constant |
|---|---|---|---|---|---|
| 37973-51-6 | 2-Phenyl-1(2)propenyl-1 ester | 2.47 | 176.22 | 8.82 | 0.44 |
| 38142-45-9 | 3-Cyclohexene-1-ethanol, 4-methyl-.beta.-methylene-, (R)- | 1.84 | 152.24 | 8.62 | 1.58 |
| 39252-02-3 | Furfuryl hexanoate | 2.38 | 196.25 | 8.80 | 2.17 |
| 39677-52-6 | 3-Methoxy Cinnamaldehyde | 1.86 | 162.19 | 8.84 | 2.49 |
| 40010-99-9 | 3-Acetyl-5-butyldihydro-2(3H)-furanone | 1.71 | 184.24 | 8.57 | 2.58 |
| 40790-29-2 | Pyrazine, 3-butyl-2,5-dimethyl- | 2.29 | 164.25 | 8.18 | 2.48 |
| 409-02-9 | Methyl Heptenone | 2.27 | 126.20 | 8.58 | 2.38 |
| 4175-66-0 | 2,5-Dimethylthiazole | 0.94 | 113.18 | 8.08 | 1.63 |
| 4180-23-8 | (E)-anethol | 2.43 | 148.20 | 8.79 | 2.34 |
| 41847-88-5 | Phenylethyl oxy-acetaldehyde | 1.55 | 164.20 | 8.61 | 2.34 |
| 42348-12-9 | 3-Ethyl-2-hydroxy-4-methylcyclopent-2-en-1-one | 0.54 | 140.18 | 9.10 | 2.58 |
| 3/5/4313 | (E,E)-2,4-heptadien-1-al | 1.98 | 110.16 | 9.00 | 2.29 |
| 6/1/4364 | Cinnamic aldehyde dimethyl acetal | 2.02 | 178.23 | 8.44 | 2.03 |
| 4501-58-0 | Campholene aldehyde | 2.2 | 152.24 | 8.31 | 1.43 |
| 4634-89-3 | cis-4-Hexenal | 1.05 | 98.14 | 9.24 | 2.26 |
| 4643-25-8 | 2-Hepten-4-one | 1.85 | 112.17 | 8.31 | 2.21 |
| 4643-27-0 | 2-Octen-4-one | 2.42 | 126.20 | 8.70 | 2.43 |
| 473-67-6 | Verbenol | 2.03 | 152.24 | 8.09 | 2.61 |
| 4748-78-1 | 4-Ethylbenzaldehyde | 2.39 | 134.18 | 9.19 | 2.54 |
| 491-04-3 | Piperitol | 2.4 | 154.25 | 8.70 | 1.72 |
| 491-09-8 | piperitenone | 2.33 | 150.22 | 8.40 | −1.20 |
| 491-31-6 | Isocoumarin | 1.69 | 146.15 | 8.63 | 2.45 |
| 491-35-0 | Lepidine | 2.46 | 143.19 | 8.13 | 2.44 |
| 11/8/4940 | ethyl maltol | 0.17 | 140.14 | 7.44 | 1.94 |
| 496-77-5 | Butyroin | 1.29 | 144.21 | 8.36 | 2.22 |
| 499-44-5 | Hinokitiol | 1.35 | 164.20 | 9.32 | 2.71 |
| 50888-63-6 | Pyrazine, 2-butyl-3,5-dimethyl- | 2.3 | 164.25 | 8.19 | 2.27 |
| 53046-97-2 | cis-3, cis-6-nonadienol | 2.45 | 140.23 | 9.52 | 2.16 |
| 53398-78-0 | trans-2-Hexenyl formate | 1.71 | 128.17 | 8.31 | 2.23 |
| 53399-81-8 | Ethyl 2-methyl-4-pentenoate | 2.26 | 142.20 | 8.16 | 2.08 |
| 536-50-5 | 1-(4-Methylphenyl)ethanol | 2 | 136.19 | 8.07 | 2.39 |
| 536-59-4 | Perillyl alcohol | 1.83 | 152.24 | 8.58 | 1.69 |
| 536-60-7 | Cumic alcohol | 2.39 | 150.22 | 8.68 | 2.39 |
| 5392-40-5 | Citral | 2.33 | 152.24 | 8.48 | −1.82 |
| 5396-89-4 | Benzyl acetoacetate | 1.43 | 192.21 | 8.05 | 1.45 |
| 12/2/5406 | p-Methylhydrocinnamic aldehyde | 2.19 | 148.20 | 9.57 | 2.84 |
| 541-58-2 | 2,4-Dimethylthiazole | 1.24 | 113.18 | 8.08 | 1.89 |
| 5426-78-8 | Acetaldehyde phenyl ethyl acetal | 2.22 | 166.22 | 8.56 | 1.83 |
| 6/6/5462 | Canthoxal | 2.16 | 178.23 | 8.80 | 2.49 |
| 6/8/5466 | Ethyl 3-mercaptopropionate | 1.36 | 134.19 | 8.92 | 1.25 |
| 5471-51-2 | Raspberry ketone | 1.58 | 164.20 | 7.67 | 1.70 |
| 554-14-3 | 2-Methylthiophene | 2.06 | 98.16 | 8.11 | 1.52 |
| 55722-59-3 | 3,6-Octadienal, 3,7-dimethyl- | 2.34 | 152.24 | 8.51 | −1.89 |
| 5577-44-6 | 2,4-Octadienal | 2.45 | 124.18 | 9.33 | 2.32 |
| 5660-60-6 | Cinnamaldehyde ethylene glycol acetal | 2.15 | 176.22 | 8.04 | 2.16 |
| 56805-23-3 | trans-3, cis-6-nonadienol | 2.45 | 140.23 | 9.52 | 2.16 |
| 57266-86-1 | 2-Heptenal, (2Z)- | 2.1 | 112.17 | 8.76 | 2.33 |
| 57500-00-2 | Methyl furfuryl disulfide | 1.92 | 160.25 | 8.19 | 2.38 |
| 579-74-8 | o-Acetylanisole | 1.55 | 150.18 | 8.40 | 1.56 |
| 58461-27-1 | Lavandulol | 1.95 | 154.25 | 8.98 | −1.82 |
| 585-74-0 | 3-Methylacetophenone | 2.27 | 134.18 | 8.23 | 1.65 |
| 589-18-4 | p-Tolyl alcohol | 1.62 | 122.17 | 8.01 | 2.35 |
| 59020-85-8 | Furfuryl thiopropionate | 1.61 | 170.23 | 8.45 | 2.16 |
| 59021-02-2 | 2-Mercaptomethylpyrazine | 0.34 | 126.18 | 8.26 | 0.66 |
| 5910-85-0 | 2,4-Heptadienal | 1.98 | 110.16 | 9.00 | 2.29 |
| 5912-86-7 | cis-iso-Eugenol | 1.85 | 164.20 | 8.60 | 2.38 |
| 5925-68-8 | S-Ethyl benzothioate | 2.21 | 152.21 | 8.74 | 1.83 |
| 5932-68-3 | trans-Isoeugenol | 1.85 | 164.20 | 8.60 | 2.38 |
| 606-27-9 | Methyl 2-nitrobenzoate | 1.57 | 181.15 | 8.45 | 2.25 |
| 606-45-1 | Methyl o-methoxybenzoate | 1.79 | 166.18 | 8.56 | 2.15 |
| 613-70-7 | Guaiacyl acetate | 1.55 | 166.18 | 8.18 | 1.57 |
| 616-44-4 | 3-Methylthiophene | 2.23 | 98.16 | 8.51 | 1.52 |
| 6191-71-5 | cis-4-Hepten-1-ol | 1.77 | 114.19 | 8.46 | 2.11 |
| 6192-44-5 | beta-Phenoxy ethyl acetate | 1.87 | 180.20 | 8.51 | 1.26 |
| 61931-81-5 | cis-3-Hexenyl lactate | 1.34 | 172.22 | 8.20 | 1.76 |
| 620-23-5 | meta-tolyl aldehyde | 2.13 | 120.15 | 8.79 | 2.38 |
| 623-15-4 | 4-(2-Furyl)-3-buten-2-one | 1.7 | 136.15 | 8.42 | 1.38 |
| 624-92-0 | Dimethyl disulfide | 1.06 | 94.19 | 8.64 | 0.27 |
| 6290-14-8 | Cyclopentyl isobutyrate | 2.29 | 156.22 | 8.42 | 2.08 |
| 6314-97-2 | Phenylacetaldehyde diethyl acetal | 2.29 | 194.27 | 9.02 | 2.37 |

-continued

| CAS Number | Name | LogP (v3.0) | Formula Weight | Odor Detection Threshold, Neural Net model | bCD Complex Stability Constant |
|---|---|---|---|---|---|
| 637-65-0 | tetrahydrofurfuryl propionate | 0.93 | 158.20 | 8.02 | 2.07 |
| 638-02-8 | 2,5-Dimethylthiophene | 2.36 | 112.19 | 8.64 | 2.04 |
| 64988-06-3 | Ethyl 2-methoxybenzyl ether | 1.98 | 166.22 | 8.23 | 2.27 |
| 65405-67-6 | p-Methoxy-alpha-methyl cinnamaldehyde | 2 | 176.22 | 8.85 | 1.16 |
| 65405-73-4 | Geranyl oxyacetaldehyde | 2.32 | 196.29 | 8.71 | −1.88 |
| 67028-40-4 | Ethyl (p-tolyloxy)acetate | 2.49 | 194.23 | 8.45 | 2.18 |
| 6728-26-3 | Trans-2-Hexenal | 1.57 | 98.14 | 8.41 | 2.26 |
| 6728-31-0 | cis-4-Heptenal | 1.85 | 112.17 | 9.51 | 2.33 |
| 67633-97-0 | 3-Mercapto-2-pentanone | 1.37 | 118.19 | 8.86 | 0.23 |
| 67634-07-5 | 3,5,6-Trimethyl-3-cyclohexene-1-carbaldehyde | 2.37 | 152.24 | 8.63 | 1.97 |
| 67634-16-6 | Floralol | 1.83 | 140.23 | 8.38 | 1.50 |
| 67634-17-7 | 2,4-Dimethyl-3-cyclohexene-1-methanol | 1.81 | 140.23 | 8.51 | 1.61 |
| 67746-30-9 | trans-2-Hexenal diethyl acetal | 2.34 | 172.27 | 8.19 | 2.13 |
| 67801-65-4 | 3,6-ivy carbaldehyde | 1.8 | 138.21 | 9.25 | 2.09 |
| 67845-46-9 | p-Methyl phenoxy acetaldehyde | 1.76 | 150.18 | 8.64 | 2.40 |
| 6789-80-6 | (Z)-3-hexen-1-al | 1.43 | 98.14 | 8.97 | 2.26 |
| 68039-48-5 | Dimethyl cyclohexene carboxaldehyde | 1.82 | 138.21 | 9.18 | 1.65 |
| 68039-49-6 | 2,4-Dimethyl-3-Cyclohexene-1-carboxaldehyde (Ligustral) | 1.78 | 138.21 | 9.24 | 1.76 |
| 68133-76-6 | cis-3-Hexenyl pyruvate | 1.9 | 170.21 | 8.50 | 1.30 |
| 68737-61-1 | 3,5-ivy carbaldehyde | 1.82 | 138.21 | 9.18 | 1.65 |
| 698-76-0 | delta-Octalactone | 2.03 | 142.20 | 8.24 | 2.83 |
| 699-10-5 | Methyl benzyl disulfide | 2.47 | 170.29 | 8.45 | 2.96 |
| 701-70-2 | 1-Phenylbutan-2-ol | 2.21 | 150.22 | 8.59 | 2.26 |
| 7452-79-1 | Ethyl 2-methylbutyrate | 1.91 | 130.19 | 7.27 | 1.75 |
| 74-93-1 | Methyl mercaptan | 0.58 | 48.10 | 8.63 | 0.43 |
| 7493-63-2 | Allyl anthranilate | 2.31 | 177.20 | 8.48 | 1.95 |
| 7493-71-2 | Allyl tiglate | 1.86 | 140.18 | 8.12 | 0.69 |
| 75-08-1 | Ethanethiol | 1.37 | 62.13 | 8.87 | 0.63 |
| 75-18-3 | dimethyl sulfide | 1.24 | 62.13 | 8.33 | 0.86 |
| 75-33-2 | 2-Propanethiol | 1.65 | 76.16 | 9.26 | 0.87 |
| 7540-51-4 | (-)-Citronellol | 2.49 | 156.27 | 8.37 | 0.64 |
| 7549-33-9 | Anisyl propionate | 2.23 | 194.23 | 8.45 | 2.08 |
| 75-66-1 | tert-Butyl mercaptan | 1.65 | 90.18 | 9.13 | 1.13 |
| 764-40-9 | 2,4-Pentadienal | 0.7 | 82.10 | 8.16 | 2.37 |
| 76649-25-7 | 3,6-Nonadien-1-ol | 2.45 | 140.23 | 9.52 | 2.16 |
| 774-48-1 | Benzaldehyde diethyl acetal | 2.03 | 180.25 | 8.57 | 2.35 |
| 7774-74-5 | 2-Thienyl mercaptan | 1.77 | 116.20 | 8.00 | 0.81 |
| 7774-79-0 | 4-(p-Tolyl)-2-butanone | 2.46 | 162.23 | 8.64 | 2.01 |
| 7774-96-1 | Isoeugenyl formate | 2.35 | 192.21 | 8.84 | 2.71 |
| 7786-44-9 | 2,6-Nonadien-1-ol | 2.43 | 140.23 | 9.59 | 2.24 |
| 7786-61-0 | 2-Methoxy-4-vinylphenol | 2.24 | 150.18 | 8.71 | 2.37 |
| 7786-67-6 | p-Menth-8-en-3-ol (8CI) | 2.48 | 154.25 | 8.42 | 2.29 |
| 81925-81-7 | filbert heptenone (Filbertone) | 2.31 | 126.20 | 8.06 | 1.92 |
| 84434-18-4 | Gardamide | 2.16 | 191.27 | 8.08 | 1.98 |
| 85-91-6 | Dimethyl anthranilate | 2.19 | 165.19 | 8.13 | 2.08 |
| 870-23-5 | Allyl mercaptan | 1.42 | 74.14 | 9.00 | 0.85 |
| 87-25-2 | Ethyl anthranilate | 2.05 | 165.19 | 8.58 | 1.84 |
| 874-66-8 | cinnamon acrolein | 1.29 | 136.15 | 8.09 | 0.92 |
| 881-68-5 | Vanillin acetate | 0.95 | 194.19 | 8.11 | 1.94 |
| 89-79-2 | Isopulegol | 2.48 | 154.25 | 8.42 | 2.29 |
| 90-02-8 | Salicylaldehyde | 1.4 | 122.12 | 8.95 | 2.21 |
| 90-05-1 | Guaiacol | 1.33 | 124.14 | 8.06 | 1.98 |
| 90-87-9 | Hydratropaldehyde dimethyl acetal | 2.12 | 180.25 | 8.60 | 2.24 |
| 91-64-5 | Coumarin | 1.68 | 146.15 | 8.55 | 2.47 |
| 928-94-9 | (Z)-2-hexen-1-ol | 1.3 | 100.16 | 8.09 | 2.06 |
| 928-95-0 | (E)-2-hexen-1-ol | 1.3 | 100.16 | 8.09 | 2.06 |
| 928-96-1 | cis-3-Hexen-1-ol | 1.3 | 100.16 | 8.06 | 2.06 |
| 93-16-3 | Methyl isoeugenol | 2.05 | 178.23 | 8.70 | 2.49 |
| 93-29-8 | Isoeugenyl acetate | 2.17 | 206.24 | 8.38 | 1.94 |
| 93-53-8 | 2-phenyl propionaldehyde | 2.06 | 134.18 | 8.43 | 2.21 |
| 93-54-9 | 1-Phenyl-1-propanol | 1.77 | 136.19 | 8.21 | 2.03 |
| 93-58-3 | Methyl benzoate | 1.86 | 136.15 | 8.03 | 2.00 |
| 93-89-0 | Ethyl benzoate | 2.25 | 150.18 | 8.60 | 2.18 |
| 93893-89-1 | Citronitrile | 2.34 | 171.24 | 8.57 | 1.27 |
| 93-92-5 | Styrallyl acetate | 2.2 | 164.20 | 8.18 | 1.54 |
| 94089-01-7 | Butanoic acid, 2-methyl-, 2-hexenyl ester, (E)- | 1.6 | 134.24 | 9.32 | 1.41 |
| 94-86-0 | Vanitrope | 2.42 | 178.23 | 8.53 | 2.39 |
| 95-20-5 | 2-Methylindole | 2.43 | 131.18 | 8.53 | 2.58 |
| 97-53-0 | Eugenol | 2.21 | 164.20 | 8.57 | 2.51 |

One grouping of perfume raw materials that have a complex stability constant of about 3.0 or less, a c Log P of about 2.5 or less, and a weight average molecular weight of about 200 Daltons or less includes beta gamma hexanol; cis 3 hexenyl acetate; ethyl-2-methyl butyrate; amyl-acetate (isomer blends); vanillin; anethole; methyl isoeugenol; guiacol; floralol; ethyl vanillin; 2,6-nonadien-1-ol; coumarin; and combinations thereof.

Another group of perfume raw materials that have a complex stability constant of about 3.0 or less, a C log P of about 2.5 or less, and a weight average molecular weight of about 200 Daltons or less includes ethyl-2-methyl butyrate; beta gamma hexanol; iso amyl acetate; amyl acetate; cis-3-Hexenyl acetate; gamma-Octalactone; ethyl vanillin; vanillin; benzaldehyde; and combinations thereof.

An additional group of perfume raw materials that have a complex stability constant of about 3.0 or less, a C log P of about 2.5 or less, and a weight average molecular weight of about 200 Daltons or less includes dimethyl anthranilate; iso-eugenyl acetate; canthoxal; 3,6-nonadien-1-ol, triplal; and combinations thereof.

Some examples of perfume raw materials with an odor detection threshold of 7−log ppb or more include can be found in the chart above.

Propellant

The compositions described herein may include a propellant. Non-limiting examples of propellants include compressed air, nitrogen, inert gases, carbon dioxide, and mixtures thereof. Propellants may also include gaseous hydrocarbons like propane, n-butane, isobutene, cyclopropane, halogenated hydrocarbons like 1,1-difluoroethane, and mixtures thereof. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42% by weight of the total fill of materials stored within the container.

Antiperspirant Active

The compositions described herein may be free of, substantially free of, or may include an antiperspirant active (i.e. any substance, mixture, or other material having antiperspirant activity). The antiperspirant active may be any particle having antiperspirant activity. The antiperspirant active is preferably insoluble in the liquid components of the antiperspirant composition. Since the amount of antiperspirant active may significantly impact skin feel, an antiperspirant composition may comprise from about 14% 16%, 18%, 20%, 22%, or 24% to about 38%, 36%, 34%, 32%, 30%, 28%, or 26% by weight of a particulate antiperspirant active. In some instances, it may be desirable to utilize a low concentration of the antiperspirant active, such as less than 20% or 18% by weight of the antiperspirant composition. The antiperspirant active concentrations refer to the anhydrous amount that is added.

Some examples of suitable antiperspirant actives include astringent metallic salts, particularly including the inorganic and organic salts of aluminum. Some non-limiting examples exemplary aluminum salts that can be used include aluminum chloride and the aluminum hydroxyhalides having the general formula $Al_2(OH)_aQ_bXH_2O$ where Q is chloride, bromide, or iodide (preferably chloride), a is from about 2 to about 5, and a+b=about 6, and a and b do not need to be integers, and where X is from about I to about 6, and X does not need to be an integer. Particularly preferred are the aluminum chlorhydroxides referred to as "5/6 basic chlorhydroxide" wherein "a" is 5 and "2/3 basic chlorhydroxide" wherein "a" is 4. Aluminum salts of this type can be prepared in the manner described more fully in U.S. Pat. Nos. 3,887,692; 3,904,741; and 4,359,456. Preferred compounds include the 5/6 basic aluminum salts of the empirical formula $Al_2(OH)_5DI2H_2O$; mixtures of $AlCl_3 6H_2O$ and $Al_2(OH)5Cl_2H_2O$ with aluminum chloride to aluminum hydroxychloride weight ratios of up to about 0.5. The antiperspirant active may be, for example, aluminum cholorohydrate.

The aluminum salt may be prepared by methods well known in the art. In some embodiments, the aluminum salts may be made by applying heat to a dilute aqueous solution of an aluminum salt (e.g., less than 20% of an aluminum salt by weight of the dilute solution) to form a solid aluminum salt comprising aluminum hydrolysis polymers. Some non-limiting examples of such methods are described in U.S. Pat. Nos. 4,871,525 and 4,359,456.

Free Perfume

In addition to any perfume that comes in as part of a cyclodextrin perfume complex, a personal aerosol composition may comprise free perfume. Free perfume is perfume that is added to the composition that is not part of a cyclodextrin perfume complex. Free perfume can be added to the composition in order to give an initial perfume. It can be the same or different than the perfume included in the cyclodextrin perfume complex. Free perfume may be added to a personal aerosol composition at a level of about 0.1% to about 20%, at a level of about 5% to about 15%, or any combination thereof, by weight of the aerosol composition.

Examples/Combinations

A. A personal aerosol composition, comprising a solvent, a cyclodextrin perfume complex, and a propellant, wherein the cyclodextrin perfume complex comprises a cyclodextrin and a perfume comprising perfume raw materials, wherein 10% or more, by weight of the perfume, of the perfume raw materials have: a cyclodextrin complex stability constant of about −2.0 to about 3.0, a C log P of about −3.0 to about 2.5; and a weight average molecular weight of about 50 Daltons to about 200.

B. The personal aerosol composition of paragraph A, wherein the cyclodextrin complex stability constant is from about −2.0 to about 2.5.

C. The personal aerosol composition paragraphs A-B, wherein the perfume raw materials are selected from the group consisting of: eugenyl formate; benzaldehyde; 2-hexen-1-yl acetate; alpha-methyl cinnamaldehyde; methyl phenylacetate; viridine; ethyl 2-phenylacetate; methyl hydrocinnamate; methyl cinnamate; 2-Phenyl-ethyl acetate; cinnamyl acetate; lilac acetaldehyde; 4-(p-Methoxyphenyl)-2-butanone; anethole; gamma-Octalactone; 3-phenyl propionaldehyde; cinnamic alcohol; cinnamic aldehyde; phenethyl formate; 3-phenyl propyl formate; isobutyl furylpropionate; styryl acetate; geranyl formate; 3-Hepten-1-ol; citronellol; trans-Geraniol; nerol; neral; melon heptenal; propyl mercaptan; 2-Propionylpyrrole; 5,6-Dimethyl-1-(1-methylethenyl)bicyclohept-5-ene-2-methanol; hydratopic alcohol; 3,4-Dimethoxyacetophenone; safranal; 2-Hydroxyacetophenone; cis-carveol, ocean propanal; Isosafrol; Indole; 2-Methylbenzothiazole; Ethyl vanillin; Vanillin; Methyl p-anisate; Benzyl propionate; 3-phenyl propyl acetate; phenyl acetaldehyde; p-Hydroxybenzaldehyde; para-anisaldehyde; Isoamyl acetate; Ethyl 3-methylthiopropionate; Methyl anthranilate; 1,2-Cyclopentanedione, 3-ethyl-; Syringaldehyde; furfuryl thioacetate; blackberry thiophenone; p-Cresyl acetate; linalool oxide (pyramid); Geranial; Parmanyl; Sorbinaldehyde; Pentyl 2-furyl ketone; m-Guaiacol; alpha-Methylcinnamic alcohol; Ethyl cyclohex-3-enecarboxylate; 2,4-Hexadienyl acetate; 4-Hydroxy-3-methylbenzaldehyde; Furan, 3-methyl-2-(3-methyl-2-butenyl)-; n-Pentyl acetoacetate; Ethyl 2-hexenoate; 2-Ethyl-4-methylthiazole; tropical thiazole; Trifernal; Coumarone; 2,4-Hexadienyl propionate; Cyclopentyl mercaptan; 2-Methyl-2-butanethiol; trans-2-Methyl-2-pentenoic acid; 2-Hexyl-1,3-dioxolane; cis-3-Hepten-1-ol; 3-Hexenyl acetate; Trans,trans-2,4-Hexadien; methyl trans-cinnamate 99%; 4-Methyl-5-vinylthiazole; 2-Propylthiazole; (S),(−)-Perillaaldehyde; 2-(1-Methylpropyl)thiazole; (+)-p-menth-1-en-9-OL 97% (mixture of isomers); Isobutyl thiazole; trans-2-Heptenal; (1S)-(−)-cis-Verbenol; Anapear; alpha-Campholenic alcohol; Ethyl 2-mercaptopropionate; 2-Methylphenethyl alcohol; Methyl 4-phenylbutyrate; Allyl crotonate; Allyl butyrate; Benzyl lactate; Vanillin isobutyrate; perillaldehyde; Neryl Formate; Allyl methyl disulfide; Methyl propyl disulfide; 2-Cyclopenten-1-one, 2-hydroxy-3,4-dimethyl-; 3-Ethyl-2-hydroxy-2-cyclopenten-1-one; 2-Octenol-1; Tetrahydrofurfuryl butyrate; Allo-ocimenol; 7-Octene-1,6-diol, 3,7-dimethyl-; 3-Ethoxybenzaldehyde; 2-Ethylbenzaldehyde; 2-hexen-1-ol; Phenoxyethyl propionate; Nerolione; 7-Methylcoumarin; Butylacrolein; 2-Hexen-1-yl acetate; Ethyl phenoxyacetate; Ethyl trans-3-hexenoate; N-Acetyl methyl anthranilate; Ethyl trans-2-hexenoate; Vertoliff; (2E,6Z)-Nona-2,6-dien-1-ol; Ocimenol; 2,6-Dimethyl-1,5,7-octatrienol-3; p-Menth-1-ene-9-al; 2,4-Octadien-1-al; Propyl anthranilate; 2-Pentanoylfuran; 4-Ethyl-2-methylthiazole; Jasmolactone; cis-3-Hexenyl formate; 1-Octenol-3; 4,5-Dimethylthiazole; 4,4-Dimethyl-5-isopropyl-1,3-dioxolane; 1-Hexen-3-yl acetate; Furfuryl valerate; 2,6-Dimethyl-6-hepten-1-ol; cis-3-Hexenyl acetate; trans-3-Hexenyl acetate; 5-Ethyl-2-thiophenecarbaldehyde; 2-Phenyl-1(2) propenyl-1 ester; 3-Cyclohexene-1-ethanol, 4-methyl-beta-methylene-, (R)—; Furfuryl hexanoate; 3-methoxy cinnamaldehyde; 3-Acetyl-5-butyldihydro-2(3H)-furanone; Pyrazine, 3-butyl-2,5-dimethyl-; Methyl Heptenone; 2,5-Dimethylthiazole; (E)-anethol; Phenylethyl oxy-acetaldehyde; 3-Ethyl-2-hydroxy-4-methylcyclopent-2-en-1-one; (E,E)-2,4-heptadien-1-al; Cinnamic aldehyde dimethyl acetal; Campholene aldehyde; cis-4-Hexenal; 2-Hepten-4-one; 2-Octen-4-one; Verbenol; 4-Ethylbenzaldehyde; Piperitol; piperitenone; Isocoumarin; Lepidine; ethyl maltol; Butyroin; Hinokitiol; Pyrazine, 2-butyl-3,5-dimethyl-; cis-3, cis-6-nonadienol; trans-2-Hexenyl formate; Ethyl 2-methyl-4-pentenoate; 1-(4-Methylphenyl)ethanol; Perillyl alcohol; Cumic alcohol; citral; Benzyl acetoacetate; p-Methylhydrocinnamic aldehyde; 2,4-Dimethylthiazole; Acetaldehyde phenyl ethyl acetal; Canthoxal; Ethyl 3-mercaptopropionate; Raspberry ketone; 2-Methylthiophene; 3,6-Octadienal, 3,7-dimethyl-; 2,4-Octadienal; Cinnamaldehyde ethylene glycol acetal; trans-3, cis-6-nonadienol; 2-Heptenal, (2Z)—; Methyl furfuryl disulfide; o-Acetylanisole; Lavandulol; 3-Methylacetophenone; p-Tolyl alcohol; Furfuryl thiopropionate; 2-Mercaptomethylpyrazine; 2,4-Heptadienal; cis-iso-Eugenol; S-Ethyl benzothioate; trans-Isoeugenol; Methyl 2-nitrobenzoate; Methyl o-methoxybenzoate; Guaiacyl acetate; 3-Methylthiophene; cis-4-Hepten-1-ol; beta-Phenoxy ethyl acetate; cis-3-Hexenyl lactate; meta-tolyl aldehyde; 4-(2-Furyl)-3-buten-2-one; Dimethyl disulfide; Cyclopentyl isobutyrate; Phenylacetaldehyde diethyl acetal; tetrahydrofurfuryl propionate; 2,5-Dimethylthiophene; Ethyl 2-methoxybenzyl ether; p-Methoxy-alpha-methyl cinnamaldehyde; Geranyl oxyacetaldehyde; Ethyl (p-tolyloxy) acetate; Trans-2-Hexenal; cis-4-Heptenal; 3-Mercapto-2-pentanone; 3,5,6-Trimethyl-3-cyclohexene-1-carbaldehyde; Floralol; 2,4-Dimethyl-3-cyclohexene-1-methanol; trans-2-Hexenal diethyl acetal; 3,6-ivy carbaldehyde; p-Methyl phenoxy acetaldehyde; (Z)-3-hexen-1-al; Dimethyl cyclohexene carboxaldehyde; 2,4-Dimethyl-3-Cyclohexene-1-carboxaldehyde; cis-3-Hexenyl pyruvate; 3,5-ivy carbaldehyde; delta-Octalactone; Methyl benzyl disulfide; 1-Phenylbutan-2-ol; Ethyl 2-methylbutyrate; Methyl mercaptan; Allyl anthranilate; Allyl tiglate; Ethanethiol; dimethyl sulfide 2-Propanethiol; (−)-Citronellol; Anisyl propionate; tert-Butyl mercaptan; 2,4-Pentadienal; 3,6-Nonadien-1-ol; Benzaldehyde diethyl acetal; 2-Thienyl mercaptan; 4-(p-Tolyl)-2-butanone; Isoeugenyl formate; 2,6-Nonadien-1-ol; 2-Methoxy-4-vinylphenol; p-Menth-8-en-3-ol; filbert heptenone; Gardamide; Dimethyl anthranilate; Allyl mercaptan; Ethyl anthranilate; cinnamon acrolein; Vanillin acetate; Isopulegol; Salicylaldehyde; Guaiacol; Hydratropaldehyde dimethyl acetal; Coumarin (Z)-2-hexen-1-ol; (E)-2-hexen-1-ol; cis-3-Hexen-1-ol; Methyl isoeugenol; Isoeugenyl acetate; 2-phenyl propionaldehyde; 1-Phenyl-1-propanol; Methyl benzoate; Ethyl benzoate; Citronitrile; Styrallyl acetate; Butanoic acid, 2-methyl-, 2-hexenyl ester, (E)-; Vanitrope; 2-Methylindole; Eugenol; and a combination thereof.

D. The personal aerosol composition of paragraphs A-B, wherein the perfume raw materials are selected from the group consisting of: beta gamma hexanol; cis 3 hexenyl acetate; ethyl-2-methyl butyrate; amyl-acetate; vanillin; anethole; methyl isoeugenol; guaiacol; floralol; 2,6-nonadien-1-ol; coumarin; and a combination thereof.

E. The personal aerosol composition of any of paragraphs A-B, wherein the perfume raw materials comprise dimethyl anthranilate; iso-eugenyl acetate; canthoxal; 3,6-nonadien-1-ol, triplal; or a combination thereof F. The personal aerosol composition of any of paragraphs A-B, wherein the perfume raw materials comprise ethyl-2-methyl butyrate; beta gamma hexanol; iso amyl acetate; amyl acetate; cis-3-hexenyl acetate; gamma-octalactone; ethyl vanillin; vanillin; benzaldehyde; or a combination thereof G. The personal aerosol composition of any of paragraphs A-F, wherein 10% or more of the perfume raw materials have an Odor Detection Threshold of about 7 or more −log molar concentration.

H. The personal aerosol composition of any of paragraphs A-G, wherein 10% or more of the perfume raw materials have an Odor Detection Threshold of about 7 to about 11.5−log molar concentration.

I. The personal aerosol composition of any of paragraphs A-H, wherein about 20% to about 100%, by weight of the perfume, of the perfume raw materials have: a complex stability constant of about −2.0 to about 3.0, a C log P of about −3.0 to about 2.5; and a weight average molecular weight of about 50 Daltons to about 200.

J. The personal aerosol composition of any of paragraphs A-I, wherein about 50% to about 100%, by weight of the perfume, of the perfume raw materials have: a complex stability constant of about −2.0 to about 3.0, a C log P of about −3.0 to about 2.5; and a weight average molecular weight of about 50 Daltons to about 200.

K. The personal aerosol composition of any of paragraphs A-J, wherein the perfume raw materials have a complex stability constant of about −1.5 to about 2.5.

L. The personal aerosol composition of any of paragraphs A-K, wherein the perfume raw materials have a C log P of about 2.0 or less.

M. The personal aerosol composition of any of paragraphs A-L, wherein the perfume raw materials have a weight average molecular weight of about 180 Daltons or less.

N. The personal aerosol composition of any of paragraphs A-M, wherein the cyclodextrin comprises an alpha-cyclodextrin, a beta-cyclodextrin, a gamma-cyclodextrin, or a combination thereof O. The personal aerosol composition of any of paragraphs A-N, wherein the cyclodextrin comprises hydroxypropyl alpha-cyclodextrin, hydroxypropyl beta-cyclodextrin, methylated-alpha-cyclodextrin, methylated-beta-cyclodextrin, or a combination thereof.

P. The personal aerosol composition of any of paragraphs A-O, wherein the percent of the perfume that is complexed with the cyclodextrin is about 75% or more.

Q. The personal aerosol composition of any of paragraphs A-P, wherein the percent of the perfume that is complexed with the cyclodextrin is about 95% or more.

R. The personal aerosol composition of any of paragraphs A-Q, wherein 10% or more of the perfume raw materials have an Odor Detection Threshold of about 7 or more −log molar concentration.

S. The personal aerosol composition of any of paragraphs A-Q, wherein 10% or more of the perfume raw materials have an Odor Detection Threshold of about 7 to about 11.5−log molar concentration.

T. The personal aerosol composition of any of paragraphs A-S, wherein about 20% to about 100%, by weight of the perfume, of the perfume raw materials have: a complex stability constant of about −2.0 to about 3.0, a C log P of about −3.0 to about 2.5; and a weight average molecular weight of about 50 Daltons to about 200.

U. The personal aerosol composition of any of paragraphs A-T, wherein about 50% to about 100%, by weight of the perfume, of the perfume raw materials have: a complex stability constant of about −2.0 to about 3.0, a C log P of about −3.0 to about 2.5; and a weight average molecular weight of about 50 Daltons to about 200.

V. The personal aerosol composition of any of paragraphs A-U, wherein the perfume raw materials have a complex stability constant of about −1.5 to about 2.5.

W. The personal aerosol composition of any of paragraphs A-V, wherein the perfume raw materials have a C log P of about 2.0 or less.

X. The personal aerosol composition of any of paragraphs A-W, wherein the perfume raw materials have a weight average molecular weight of about 180 Daltons or less.

Y. A personal aerosol composition, comprising a solvent, a cyclodextrin perfume complex, and a propellant, wherein the cyclodextrin perfume complex comprises a cyclodextrin and a perfume comprising perfume raw materials and wherein 20% or more, by weight of the perfume, of the perfume raw materials, are selected from the group consisting of: ethyl-2-methyl butyrate; beta gamma hexanol; iso amyl acetate; amyl acetate; cis-3-hexenyl acetate; gamma-octalactone; ethyl vanillin; vanillin; benzaldehyde; dimethyl anthranilate; iso-eugenyl acetate; canthoxal; 3,6-nonadien-1-ol, triplal; and combinations thereof.

Z. The personal aerosol composition of paragraph Y, wherein the perfume raw materials are selected from the group consisting of ethyl-2-methyl butyrate; beta gamma hexanol; iso amyl acetate; amyl acetate; cis-3-hexenyl acetate; gamma-octalactone; ethyl vanillin; vanillin; benzaldehyde; and combinations thereof.

AA. The personal aerosol composition of paragraph Y, wherein the perfume raw materials are selected from the group consisting of dimethyl anthranilate; iso-eugenyl acetate; canthoxal; 3,6-nonadien-1-ol, triplal; and combinations thereof.

BB. The personal aerosol composition of any of paragraphs Y-AA, wherein about 20% to about 100%, by weight of the perfume, of the perfume raw materials have: a complex stability constant of about −2.0 to about 3.0, a C log P of about −3.0 to about 2.5; and a weight average molecular weight of about 50 Daltons to about 200.

CC. The personal aerosol composition of any of paragraphs Y-BB, wherein about 50% to about 100%, by weight of the perfume, of the perfume raw materials have: a complex stability constant of about −2.0 to about 3.0, a C log P of about −3.0 to about 2.5; and a weight average molecular weight of about 50 Daltons to about 200.

DD. The personal aerosol composition of any of paragraphs Y-CC, wherein about 50% to about 100% of the perfume raw materials have a complex stability constant of about −1.5 to about 2.5.

EE. The personal aerosol composition of any of paragraphs Y-DD, wherein about 50% to about 100% of the perfume raw materials have a C log P of about 2.0 or less.

FF. The personal aerosol composition of any of paragraphs Y-EE, wherein about 20% to about 100% of the perfume raw materials have a weight average molecular weight of about 180 Daltons or less.

GG. The personal aerosol composition of any of paragraphs Y-FF, wherein the perfume is part of a cyclodextrin complex.

HH. The personal aerosol composition of any of paragraphs Y-GG, wherein the cyclodextrin comprises an alpha-cyclodextrin, a beta-cyclodextrin, a gamma-cyclodextrin, or a combination thereof.

II. The personal aerosol composition of any of paragraphs Y-HH, wherein the cyclodextrin comprises hydroxypropyl alpha-cyclodextrin, hydroxypropyl beta-cyclodextrin, methylated-alpha-cyclodextrin, methylated-beta-cyclodextrin, or a combination thereof JJ. The personal aerosol composition of any of paragraphs Y-II, wherein the percent of the perfume that is complexed with the cyclodextrin is about 75%.

KK. The personal aerosol composition of any of paragraphs Y-JJ, wherein the percent of the perfume that is complexed with the cyclodextrin is about 95% or more.

LL. The personal aerosol composition of any of paragraphs Y-KK, wherein the cyclodextrin comprises beta-cyclodextrin.

Examples

Exemplary perfume compositions in accordance with the invention can include:

| Material | % by weight of perfume composition |
|---|---|
| Cis-3-hexen-1-ol | 5-50% |
| Cis-3-hexenyl acetate | 5-50% |
| Ethyl 2-methylbutyrate | 5-50% |
| Isoamyl acetate | 5-50% |
| Vanillin | 5-50% |

Additional information about the perfume raw materials in the example can be found in the table below:

| CAS Number | Name | cLogP | Weight average molecular weight (Dalton) | Odor Detection threshold (-log molar concentration) | Cyclodextrin stability constant (log K) |
|---|---|---|---|---|---|
| 123-92-2 | Isoamyl acetate | 1.87 | 130 | 7.12 | 0.33 |
| 121-33-5 | Vanillin | 1.04 | 152 | 9.93 | 1.36 |
| 7452-79-1 | Ethyl 2-methylbutyrate | 1.91 | 130 | 7.27 | 0.75 |
| 928-96-1 | Cis-3-hexen-1-ol | 1.3 | 100 | 8.06 | 1.06 |
| 3681-71-8 | Cis-3-hexenyl acetate | 2.18 | 142 | 8.16 | 0.48 |

The perfume composition can be made by blending all of the perfume raw materials together until a homogenous solution is formed.

This exemplary composition can then be formed into a cyclodextrin complex by mixing 10 parts cyclodextrin with 10 (or more) parts water, and 1 part (or less) of the perfume composition. After the mixing, the slurry will be more viscous than at the start of mixing—the change in viscosity is believed to be due to the formation of the cyclodextrin perfume complex. The mixture is then dried (or spray dried) to remove the water and leave the cyclodextrin and perfume complex as a powder.

Exemplary Antiperspirant Spray with Propellant

| Raw Material Name | % W/W |
|---|---|
| Propellant (Isobutane Propane) | 84.90 |
| XiameterPMX-0245 Cyclopentasiloxane | 7.67 |
| Achieve DA1100 Aluminum Chlorohydrate | 3.83 |
| Free Fragrance | 1.84 |
| Beta Cyclodextrin perfume complex | 0.77 |
| Disteardimonium Hectorite | 0.46 |
| Dow Corning Dimethicone 50 cst | 0.38 |
| triethyl citrate | 0.15 |
| Total | 100.00 |

The Exemplary Antiperspirant Spray with Propellant can be prepared by mixing a first portion of the cyclopentasiloxane and dimethicone, and disteardimonium hectorite by lightly stirring followed by milling for at least 1 minute using a single head Silverson mill. The triethyl citrate is added next followed by at least five minutes of milling, followed by addition of the aluminum chlorohydrate, a second portion of the cyclopentasiloxane and dimethicone, the beta cyclodextrin perfume complex, and free fragrance. After making the composition, approximately 20 gms thereof is added to a clear glass aerosol bottle (Part # ATL-SC4-48 available from Aero-Tech Laboratory Equipment Co of USA). The glass bottle is sealed with a valve assembly and then approximately 40 gms of isobutane propellant is added to the bottle thru the valve assembly.

In Vitro Perfume Release Method

Released Perfume (RP) Sample

About 500 milligrams of a cyclodextrin perfume complex is weighed into a glass scintillation vial. About 1 milliliter of water is added to the vial. The vial is then capped tightly and vortexed for about 30 seconds to create a slurry. The RP sample is then placed into a 37 degrees Celsius oven to incubate for 4 hours. The sample vial is removed from the oven and allowed to cool to room temperature. 10 milliliters of hexane is then added to the vial. The vial is capped tightly and mixed by hand shaking for about 10 seconds and then mixed on high speed with a vortex mixer for about 30 seconds to extract perfume components liberated by the water incubation step. After allowing solids to settle, an aliquot of the sample is transferred to a 2 milliliter autosampler vial for analysis.

Total Perfume (TP) Sample

Another 500 milligrams of the same cyclodextrin perfume complex used to create the RP sample is weighed into a scintillation vial. About 10 milliliters of acetone is added to the vial. This sample is then capped tightly and vortexed for about 30 seconds to disperse the sample. The total sample is then placed into a 70 degrees Celsius oven for 4 hours. The sample is removed from the oven and allowed to cool to room temperature. After allowing solids to settle, an aliquot of the sample is transferred to a 2 milliliter autosampler vial for analysis.

Analysis

The RP and TP samples are analyzed using liquid injection gas chromatography with a mass selective detector. The injection port is heated to 270 degrees Celsius and operated in split mode with a split ratio of about 20:1. The carrier gas is helium and delivered at a constant flowrate of about 1.2 milliliters per minute. The oven temperature is ramped from an initial temperature of 50 degrees Celsius to a final temperature of 250 degrees Celsius at a rate of 10 degrees Celsius per minute. The final temperature is held for 2 minutes. The mass selective detector is operated in scanning mode and perfume components are identified using NIST mass spectral library searching. The chromatogram from the TP sample is used to identify a specific mass to charge ratio for each perfume component and extracted ion peak areas for each perfume component are obtained. The RP chromatogram is correspondingly processed.

Results Calculation

Individual perfume component peak areas per unit of sample weight from the RP sample are divided by the corresponding peak areas per unit of sample weight from the TP sample. The resulting ratio is multiplied by 100 to calculate a release percentage for each individual perfume material. The release percentages from all perfume components are averaged to calculate a composite release value for a given complex sample.

Finished Product Testing

Where the ability to test the cyclodextrin perfume complex itself is not available, one can test for perfume release from a cyclodextrin perfume complex contained in a finished product as set out below.

Finished Product Testing

In duplicate, 50 milligrams of finished product personal aerosol composition is weighed onto a 1.5×3 centimeters strip of aerosol testing paper manufactured by Orlandi. The samples are allowed to sit on a laboratory benchtop for at least 72 hours to allow volatile matrix components and parent perfume to evaporate. One of the treated strips is transferred—in its dry condition—to a 20 milliliter headspace vial and capped tightly. The other sample strip is sprayed with a fine mist of about 20 milligrams of water and then transferred into a separate 20 milliliter headspace vial and capped tightly. The headspace sample vials are allowed to equilibrate for about 2 hours and then transferred to the gas chromatograph for analysis.

Analysis

The samples are analyzed using headspace solid phase microextraction (SPME) gas chromatography with a mass selective detector. The headspace samples are incubated at about 30 degrees Celsius for 10 minutes. The headspace is then sampled using a Supelco 50/30 μm divinylbenzene/Carboxen on polydimethylsiloxane 1 centimeter SPME fiber for 1 minute. The autosampler desorbs the fiber in the injection port, which is heated to 270 degrees Celsius and operated in splitless mode. The carrier gas is helium and delivered at a constant flowrate of about 1.2 milliliters per minute. The oven temperature is ramped from an initial temperature of 50 to a final temperature of 250 degrees Celsius at a rate of 10 degrees Celsius per minute. The final temperature is held for 2 minutes. The mass selective detector is operated in scanning mode and perfume components are identified using NIST mass spectral library searching.

Chromatogram Evaluation

The total ion chromatogram from the wetted sample is overlaid with the total ion chromatogram from the dry sample. Chromatographic peaks that are observed only from the wetted sample are a result of perfume components being released from a perfume delivery technology that is activated by water. These perfume components can then be identified using a mass spectral library such as NIST.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal aerosol composition, comprising an antiperspirant active, from about 15% to about 80%, by weight of the composition, of a non-volatile solvent, from about 0.1% to about 10%, by weight of the composition, of a cyclodextrin perfume complex, from about 2% to about 8%, by weight of the composition, of a volatile solvent, and a propellant, wherein the cyclodextrin perfume complex comprises a cyclodextrin and a perfume comprising perfume raw materials, wherein 10% or more, by weight of the perfume, of the perfume raw materials have:
   a) a cyclodextrin complex stability constant (log k) of about 3.0 or less,
   b) a ClogP of about 2.5 or less; and
   c) a weight average molecular weight of about 200 Daltons or less;
   and wherein the percent of the perfume, by weight, that is complexed with the cyclodextrin is greater than about 95% and wherein the cyclodextrin complex is spray dried.

2. The personal aerosol composition of claim 1, wherein the cyclodextrin complex stability constant (log k) is from about −2.0 to about 2.5.

3. The personal aerosol composition of claim 1, wherein the perfume raw materials are selected from the group consisting of: beta gamma hexanol; cis 3 hexenyl acetate; ethyl-2-methyl butyrate; amyl-acetate; vanillin; anethole; methyl isoeugenol; guaiacol; floralol; 2,6-nonadien-1-ol; coumarin; and a combination thereof.

4. The personal aerosol composition of claim 1, wherein the perfume raw materials comprise dimethyl anthranilate; iso-eugenyl acetate; canthoxal; 3,6-nonadien-1-ol, triplal; or a combination thereof.

5. The personal aerosol composition of claim 1, wherein the perfume raw materials comprise ethyl-2-methyl butyrate; beta gamma hexanol; iso amyl acetate; amyl acetate; cis-3-hexenyl acetate; gamma-octalactone; ethyl vanillin; vanillin; benzaldehyde; or a combination thereof.

6. The personal aerosol composition of claim 1, wherein the 10% or more of the perfume raw materials also have an Odor Detection Threshold of about 7 or more −log molar concentration.

7. The personal aerosol composition of claim 1, wherein about 20% to about 100%, by weight of the perfume, of the perfume raw materials have: a complex stability constant of about 3.0 or less, a C log P of about 2.5 or less; and a weight average molecular weight of about 200 Daltons or less.

8. The personal aerosol composition of claim 1, wherein the perfume raw materials have a complex stability constant of about −1.5 to about 2.5.

9. The personal aerosol composition of claim 1, wherein the cyclodextrin comprises an alpha-cyclodextrin, a beta-cyclodextrin, a gamma-cyclodextrin, or a combination thereof.

10. The personal aerosol composition of claim 1, wherein the cyclodextrin comprises hydroxypropyl alpha-cyclodextrin, hydroxypropyl beta-cyclodextrin, methylated-alpha-cyclodextrin, methylated-beta-cyclodextrin, or a combination thereof.

11. The personal aerosol composition of claim 1, wherein the cyclodextrin comprises beta cyclodextrin.

* * * * *